United States Patent
Ohtsuka et al.

(10) Patent No.: US 9,846,028 B2
(45) Date of Patent: Dec. 19, 2017

(54) FILM THICKNESS MEASUREMENT METHOD AND FILM THICKNESS MEASUREMENT DEVICE

(71) Applicant: HAMAMATSU PHOTONICS K.K., Hamamatsu-shi, Shizuoka (JP)

(72) Inventors: Kenichi Ohtsuka, Hamamatsu (JP); Tetsuhisa Nakano, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/114,909

(22) PCT Filed: Oct. 24, 2014

(86) PCT No.: PCT/JP2014/078385
§ 371 (c)(1),
(2) Date: Jul. 28, 2016

(87) PCT Pub. No.: WO2015/114895
PCT Pub. Date: Aug. 6, 2015

(65) Prior Publication Data
US 2016/0349038 A1    Dec. 1, 2016

(30) Foreign Application Priority Data
Jan. 30, 2014   (JP) ................. 2014-015973

(51) Int. Cl.
*G01B 11/06* (2006.01)
*G01N 21/27* (2006.01)

(52) U.S. Cl.
CPC ...... *G01B 11/0625* (2013.01); *G01B 11/0691* (2013.01); *G01N 21/27* (2013.01)

(58) Field of Classification Search
CPC  G01B 11/0608; G01B 11/0625; G01B 15/02; G01N 1/4077; G01N 2001/4088;
(Continued)

(56) References Cited

U.S. PATENT DOCUMENTS

| | | | | |
|---|---|---|---|---|
| 2007/0109551 | A1* | 5/2007 | Aiyer | G01B 11/0675 356/485 |
| 2008/0049222 | A1* | 2/2008 | Yamaguchi | G01B 11/0625 356/328 |
| 2013/0155390 | A1* | 6/2013 | Jensen | G01B 11/06 356/72 |

FOREIGN PATENT DOCUMENTS

| | | |
|---|---|---|
| JP | S58-704 A | 1/1983 |
| JP | H05-248824 A | 9/1993 |

(Continued)

OTHER PUBLICATIONS

Filip Bruyneel, "Method for measuring the cell gap in liquid-crystal displays," Optical Engineering, Feb. 2001, doi:10.1117/1.1337036, pp. 259-267, vol. 40, No. 2.

(Continued)

*Primary Examiner* — Michael P Stafira
(74) *Attorney, Agent, or Firm* — Drinker Biddle & Reath LLP

(57) ABSTRACT

A film thickness measurement device 1A includes a light emission unit 10 for emitting light onto a measurement object 100, a light detection unit 20A for detecting the wavelength-dependent intensity of reflected light, and a film thickness calculation unit 30A for determining the film thickness of a first film 102 by comparing measured spectral reflectance obtained based on the detection result in the light detection unit 20A with theoretical spectral reflectance that takes into account front surface reflectance, front surface transmissivity, and back surface reflectance. The film thickness calculation unit 30A compares the measured spectral reflectance with a plurality of values of the theoretical spectral reflectance obtained by changing the front surface reflectance value, the front surface transmissivity value, and the back surface reflectance value, and determines the film thickness of the first film 102 based on the theoretical spectral reflectance closest to the measured spectral reflectance.

21 Claims, 12 Drawing Sheets

(58) Field of Classification Search
CPC ... G01N 2021/4166; G01N 2021/8438; G01N 21/21; G01N 21/31; G01N 21/4133; G01N 21/8422; G01N 2201/0873; G01N 22/00
See application file for complete search history.

(56) References Cited

FOREIGN PATENT DOCUMENTS

| | | |
|---|---|---|
| JP | H06-34523 A | 2/1994 |
| JP | H07-55435 A | 3/1995 |
| JP | H08-99346 A | 4/1996 |
| JP | 2000-065536 A | 3/2000 |
| JP | 2002-277215 A | 9/2002 |
| JP | 2003-202404 | 7/2003 |
| JP | 2004-191266 A | 7/2004 |
| JP | 2004-354372 A | 12/2004 |
| JP | 2005-140726 A | 6/2005 |
| JP | 2008-292473 A | 12/2008 |

OTHER PUBLICATIONS

International Preliminary Report on Patentability dated Aug. 11, 2016 for PCT/JP2014/078385.

* cited by examiner

FILM THICKNESS MEASUREMENT METHOD AND FILM THICKNESS MEASUREMENT DEVICE

TECHNICAL FIELD

The present invention relates to a film thickness measurement method and a film thickness measurement device.

BACKGROUND ART

Patent Literature 1 describes a method for manufacturing a composite film laminated with a light-transmitting thin film. Patent Literature 1 describes that, when ultrathin films are formed on both surfaces of a base film, light reflected from one of the ultrathin films formed on the back surface of the base film has an influence on measurement of the thickness of the other of the ultrathin films formed on the front surface of the base film. The method described in Patent Literature 1 is intended to reduce such an influence by mixing a light-absorbing material into the base film.

Patent Literature 2 describes a method for measuring a thickness of a thin film formed on a transparent substrate. Patent Literature 2 describes that, when a thin film formed on the front surface of the transparent substrate is irradiated with light and the thickness of the thin film is measured based on light reflected therefrom, light reflected from the back surface of the transparent substrate has an influence on the accuracy of the measurement. To solve this problem, in the measurement method described in Patent Literature 2, the thickness of the thin film is measured taking into account a back surface reflection coefficient contribution ratio γ being a ratio at which the light reflected from the back surface of the transparent substrate is detected.

Patent Literature 3 describes a method in which a multilayer thin film is irradiated with light and the thickness of the multilayer thin film is measured based on a spectrum of light reflected therefrom. In the measurement method described in Patent Literature 3, a fast Fourier transformation method is used to measure thicknesses of films on the front and back surfaces of a measurement target film in which the films are formed on both surfaces of a base material. The thicknesses of the films on the front and back surfaces are measured using reflected light in a low-transmissivity wavelength band and reflected light in a high-transmissivity wavelength band.

Patent Literature 4 describes a method for measuring a thickness of a film formed on a substrate. In the measurement method described in Patent Literature 4, so as to efficiently measure the thickness of the film on the substrate even if the roughness state of the surface of the substrate includes variations, the ratio (light-receiving ratio) of reflected light incident to a light receiving unit is calculated for each film thickness based on a relation between theoretical reflectance and light reception data in the case in which the substrate is mirror-surfaced, while changing the hypothetical value of the thickness of the film on the substrate. In addition, the light-receiving ratio and the theoretical reflectance are used to set model data of a reflected spectrum for the substrate having the hypothetical film thickness, and the model data is compared with the light reception data. Then, a film thickness corresponding to the model data with which the degree of agreement of the light reception data is the highest is identified as the thickness of the thin film.

CITATION LIST

Patent Literature

Patent Literature 1: Japanese Unexamined Patent Publication No. H8-99346
Patent Literature 2: Japanese Unexamined Patent Publication No. 2000-65536
Patent Literature 3: Japanese Unexamined Patent Publication No. 2008-292473
Patent Literature 4: Japanese Unexamined Patent Publication No. 2002-277215

SUMMARY OF INVENTION

Technical Problem

Examples of the method for measuring a thickness of a thin film formed on a base material include a method in which the thin film is irradiated with light to detect light reflected therefrom, and the thickness is identified based on the spectrum of the reflected light. However, there are cases in recent years in which various thin films are formed on both the front and back surfaces of a resin film or a glass base material. A transparent conductive film for use in a touchscreen panel can be cited as an example, in which a clear hard coat is applied on the front surface, and an optical adjustment layer, an adhesion layer, and a transparent conductive (ITO) film are sequentially stacked on the back surface. In such a case, light reflected from the back surface side of a base material has an influence on the measurement, so that it may be difficult to accurately measure the thickness of a thin film with the method described above.

The present invention has been made in view of the problem described above, and aims at providing a film thickness measurement method and a film thickness measurement device that enable accurate measurement of the thickness of a thin film on the front surface of a base material even when thin films are formed on both the front and back surfaces of the base material.

Solution to Problem

In order to solve the problem described above, according to an aspect of the present invention, a first film thickness measurement method is a method for measuring film thicknesses of a measurement object including a base material having a front surface and a back surface, a first film formed on the front surface, and a second film formed on the back surface and includes a light emitting step of emitting light onto the front surface side of the measurement object; a light detecting step of detecting wavelength-dependent intensity of reflected light on the front surface side of the measurement object; and a film thickness identifying step of determining a film thickness of the first film by comparing measured spectral reflectance that is wavelength-dependent reflectance obtained based on the detection result at the light detecting step with theoretical spectral reflectance that is wavelength-dependent theoretical reflectance and takes into account front surface reflectance being reflectance on the front surface side, front surface transmissivity being transmissivity on the front surface side, and back surface reflectance being reflectance on the back surface side. In the first film thickness measurement method, the film thickness identifying step compares the measured spectral reflectance with a plurality of values of the theoretical spectral reflectance obtained by changing the value of the front surface reflectance, the value of the front surface transmissivity, and the value of the back surface reflectance, and determines the film thickness of the first film based on a value of the theoretical spectral reflectance closest to the measured spectral reflectance.

As described above, when the thin films are formed on both the front and back surfaces of the base material, the light reflected from the back surface side of the base material has an influence on the measurement of the thickness of the thin film on the front surface. The degree of this influence depends on the reflectance on the back surface side of the base material, and the reflectance on the back surface side of the base material changes with the refractive index and the thickness of the thin film formed on the back surface. In the first film thickness measurement method described above, the film thickness identifying step compares (fits) the measured spectral reflectance with the theoretical spectral reflectance that takes into account the reflectance on the front surface side, the transmissivity on the front surface side, and the reflectance on the back surface side; that is, in more detail, the film thickness identifying step determines the film thickness of the first film based on the value of the theoretical spectral reflectance closest to the measured spectral reflectance among the values of the theoretical spectral reflectance obtained by changing each of the value of the reflectance on the front surface side, the value of the transmissivity on the front surface side, and the value of the reflectance on the back surface side. Such a method can reflect the influence of the reflected light on the back surface side in the theoretical spectral reflectance, so that the thickness of the first film on the front surface can be accurately measured by taking into account the influence of the thickness and the refractive index of the second film formed on the back surface.

According to another aspect of the present invention, a second film thickness measurement method is a method for measuring film thicknesses of a measurement object including a base material having a front surface and a back surface, a first film formed on the front surface, and a second film formed on the back surface and includes a light emitting step of emitting light onto the front surface side of the measurement object; a light detecting step of detecting wavelength-dependent intensity of transmitted light on the back surface side of the measurement object; and a film thickness identifying step of determining a film thickness of the first film by comparing measured spectral transmissivity that is wavelength-dependent transmissivity obtained based on the detection result at the light detecting step with theoretical spectral transmissivity that is wavelength-dependent theoretical transmissivity and takes into account front surface transmissivity being transmissivity on the front surface side, front surface reflectance being reflectance on the front surface side, back surface transmissivity being transmissivity on the back surface side, and back surface reflectance being reflectance on the back surface side. In the second film thickness measurement method, the film thickness identifying step compares the measured spectral transmissivity with a plurality of values of the theoretical spectral transmissivity obtained by changing each of the value of the front surface transmissivity, the value of the front surface reflectance, the value of the back surface transmissivity, and the value of the back surface reflectance, and determines the film thickness of the first film based on a value of the theoretical spectral transmissivity closest to the measured spectral transmissivity.

In the second film thickness measurement method described above, the film thickness identifying step compares (fits) the measured spectral transmissivity with the theoretical spectral transmissivity that takes into account the transmissivity and the reflectance on the front surface side, and the transmissivity and the reflectance on the back surface side; that is, in more detail, the film thickness identifying step determines the film thickness of the first film based on the value of the theoretical spectral transmissivity closest to the measured spectral transmissivity among the values of the theoretical spectral transmissivity obtained by changing each of the value of the transmissivity on the front surface side, the value of the reflectance on the front surface side, the value of the transmissivity on the back surface side, and the value of the reflectance on the front surface side. Such a method can reflect the influence of the second film on the back surface side in the theoretical spectral transmissivity, so that the thickness of the first film on the front surface can be accurately measured by taking into account the influence of the thickness and the refractive index of the second film formed on the back surface.

According to still another aspect of the present invention, a first film thickness measurement device is a device for measuring film thicknesses of a measurement object including a base material having a front surface and a back surface, a first film formed on the front surface, and a second film formed on the back surface and includes a light emission unit for emitting light onto the front surface side of the measurement object; a light detection unit for detecting wavelength-dependent intensity of reflected light on the front surface side of the measurement object; and a film thickness calculation unit for determining a film thickness of the first film by comparing measured spectral reflectance that is wavelength-dependent reflectance obtained based on the detection result in the light detection unit with theoretical spectral reflectance that is wavelength-dependent theoretical reflectance and takes into account front surface reflectance being reflectance on the front surface side, front surface transmissivity being transmissivity on the front surface side, and back surface reflectance being reflectance on the back surface side. In the first film thickness measurement device, the film thickness calculation unit is configured to compare the measured spectral reflectance with a plurality of values of the theoretical spectral reflectance obtained by changing each of the value of the front surface reflectance, the value of the front surface transmissivity, and the value of the back surface reflectance, and to determine the film thickness of the first film based on a value of the theoretical spectral reflectance closest to the measured spectral reflectance.

In the first film thickness measurement device described above, the film thickness calculation unit compares (fits) the measured spectral reflectance with the theoretical spectral reflectance that takes into account the reflectance on the front surface side, the transmissivity on the front surface side, and the reflectance on the back surface side; that is, in more detail, the film thickness calculation unit determines the film thickness of the first film based on the value of the theoretical spectral reflectance closest to the measured spectral reflectance among the values of the theoretical spectral reflectance obtained by changing each of the value of the reflectance on the front surface side, the value of the transmissivity on the front surface side, and the value of the reflectance on the back surface side. As a result, the influence of the reflected light on the back surface side can be reflected in the theoretical spectral reflectance, so that the thickness of the first film on the front surface can be accurately measured by taking into account the influence of the thickness and the refractive index of the second film formed on the back surface.

According to still another aspect of the present invention, a second film thickness measurement device is a device for measuring film thicknesses of a measurement object including a base material having a front surface and a back surface, a first film formed on the front surface, and a second film formed on the back surface includes a light emission unit for emitting light onto the front surface side of the measurement object; a light detection unit for detecting wavelength-dependent intensity of transmitted light on the back surface side of the measurement object; and a film thickness calculation unit for determining a film thickness of the first film by comparing measured spectral transmissivity that is wavelength-dependent transmissivity obtained based on the detection result in the light detection unit with theoretical spectral transmissivity that is wavelength-dependent theoretical transmissivity and takes into account front surface transmissivity being transmissivity on the front surface side, front surface reflectance being reflectance on the front surface side, back surface transmissivity being transmissivity on the back surface side, and back surface reflectance being reflectance on the back surface side. In the second film thickness measurement device, the film thickness calculation unit is configured to compare the measured spectral transmissivity with a plurality of values of the theoretical spectral transmissivity obtained by changing each of the value of the front surface transmissivity, the value of the front surface reflectance, the value of the back surface transmissivity, and the value of the back surface reflectance, and to determine the film thickness of the first film based on a value of the theoretical spectral transmissivity closest to the measured spectral transmissivity.

In the second film thickness measurement device described above, the film thickness calculation unit compares (fits) the measured spectral transmissivity with the theoretical spectral transmissivity that takes into account the transmissivity on the front surface side, the reflectance on the front surface side, and the transmissivity on the back surface side, and the reflectance on the back surface side; that is, in more detail, the film thickness calculation unit determines the film thickness of the first film based on the value of the theoretical spectral transmissivity closest to the measured spectral transmissivity among the values of the theoretical spectral transmissivity obtained by changing each of the value of the transmissivity on the front surface side, the value of the reflectance on the front surface side, the value of the transmissivity on the back surface side, and the value of the reflectance on the back surface side. As a result, the influence of the second film on the back surface side can be reflected in the theoretical spectral transmissivity, so that the thickness of the first film on the front surface can be accurately measured by taking into account the influence of the thickness and the refractive index of the second film formed on the back surface.

The method described in Patent Literature 1 has the problem that the measurement object is limited because the light-absorbing material needs to be mixed into the base film. Such a method cannot be used when, in particular, a transparent base film, such as the transparent conductive film described above, is used. In contrast, any of the film thickness measurement methods and the film thickness measurement devices described above allows the film thickness to be accurately measured regardless of the light transmittance of the base material when the films are formed on both surfaces of the base material.

In the method described in Patent Literature 2, obtaining the back surface reflection coefficient contribution ratio γ requires both measurement of a reflected spectrum when the film is not formed and measurement of a reflected spectrum in the state in which the reflection from the back surface of the base material is restrained by using, for example, a light trap, thus spending time and effort for the measurement. In contrast, any of the film thickness measurement methods and the film thickness measurement devices described above simply requires only the measurement of the wavelength-dependent reflectance (or the wavelength-dependent transmissivity), so that the film thickness can be measured in a simple manner when the films are formed on both surfaces of the base material.

A method using the fast Fourier transformation method, such as the method described in Patent Literature 3, is not suitable for measuring the thickness of a thin film having a thickness of, for example, 1 μm. Any of the film thickness measurement methods and the film thickness measurement devices described above allows such a very thin film to be accurately measured in thickness. The method described in Patent Literature 3 is difficult to be used to accurately measure the film thickness when the film includes a plurality of layers having refractive indices different from each other. In contrast, any of the film thickness measurement methods and the film thickness measurement devices described above allows the film thickness to be accurately measured even when the first and second films each include a plurality of layers.

Advantageous Effects of Invention

A film thickness measurement method and a film thickness measurement device according to aspects of the present invention allow the thickness of a thin film on the front surface of a base material to be accurately measured even when thin films are formed on both the front and back surfaces of the base material.

DESCRIPTION OF EMBODIMENTS

Embodiments of a film thickness measurement method and a film thickness measurement device according to one aspect of the present invention will be described below in detail with reference to the accompanying drawings. In the description of the drawings, the same components are denoted by the same reference signs, and duplicate description thereof will be omitted.

First Embodiment

Figure 1:
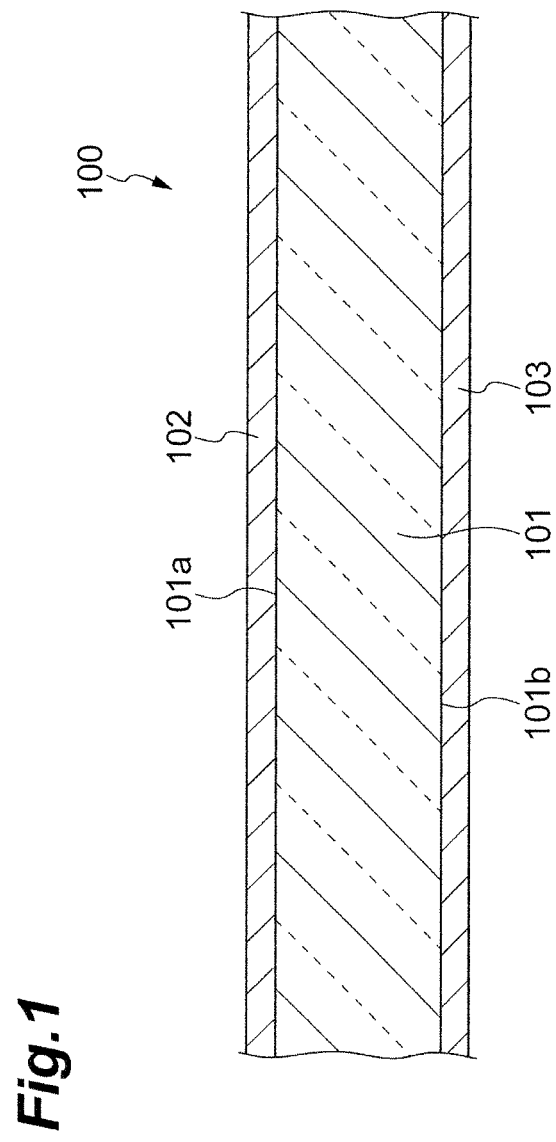
FIG. 1 is a sectional view showing the configuration of a measurement object of a film thickness measurement method and a film thickness measurement device according to a first embodiment of the present invention.

FIG. 1 is a sectional view showing the configuration of a measurement object 100 of a film thickness measurement method and a film thickness measurement device according to a first embodiment of the present invention. As shown in FIG. 1, the measurement object 100 includes a base material 101, a first film (front surface film) 102, and a second film (back surface film) 103. The base material 101 is a plate-like or film-like member having a front surface 101a and a back surface 101b, and is constituted by, for example, a resin, glass, or a semiconductor wafer. The thickness of the base material 101 is, for example, 100 µm or larger. The first film 102 is formed on the front surface 101a of the base material 101. The second film 103 is formed on the back surface 101b of the base material 101. The first and second films 102 and 103 are formed by a process of, for example, film formation such as a vacuum film formation, coating, or etching. Examples of the measurement object 100 include a touchscreen panel, a semiconductor device, a secondary cell, a solar cell, a flat panel display (FPD), and an optical film. If the measurement object 100 is a transparent conductive film for use in a touchscreen panel, the first film 102 includes a plurality of layers, such as an optical adjustment layer, an adhesion layer, and a transparent conductive (ITO) film, and the second film 103 is constituted by a layer of a clear hard coating agent.

Figure 2:
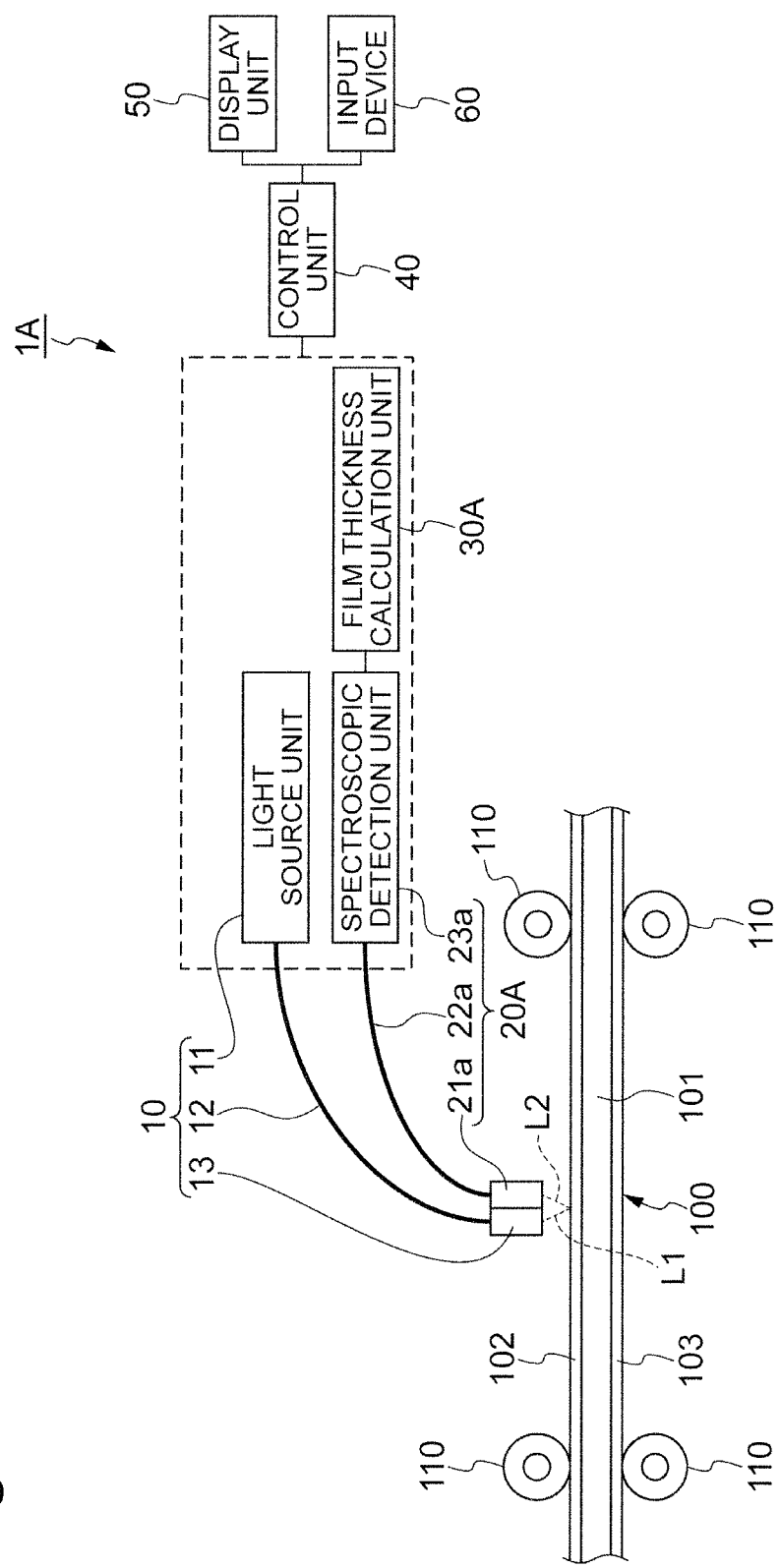
FIG. 2 is a diagram schematically showing the configuration of the film thickness measurement device according to the first embodiment.

FIG. 2 is a diagram schematically showing the configuration of a film thickness measurement device 1A according to the present embodiment. The film thickness measurement device 1A is a device for measuring the film thickness of the measurement object 100 shown in FIG. 1. As shown in FIG. 2, the film thickness measurement device 1A includes a light emission unit 10, a light detection unit 20A, and a film thickness calculation unit 30A. The measurement object 100 may be in the state of being conveyed by rollers 110 as shown in FIG. 2, or may be stationary.

The light emission unit 10 emits light onto a surface on the front surface 101a side of the measurement object 100. The light emission unit 10 includes a light source 11, a light guiding member 12, and a light emitting part 13. The light source 11 generates incoherent light L1. The wavelength band of the light L1 may be a visible wavelength band. In that case, the light source 11 is suitably, for example, a lamp-based light source or a white LED for emitting white light. The wavelength band of the light L1 may be a wavelength band ranging from the visible wavelength band to a near-infrared wavelength band, or may have a substantially flat (broad) spectrum in the infrared wavelength range. In particular, when the wavelength band of the light L1 includes the near-infrared wavelength band, the light L1 can pass through the measurement object 100 even if the measurement object 100 is colored. Hence, the influence of the coloring of the measurement object 100 can be reduced. In that case, various light-emitting components, such as an amplified spontaneous emission (ASE) light source, an LED, and a superluminescent diode (SLD) can be used as the light source 11. Optical components, such as a white light source and an optical film, may be combined with one another.

The light guiding member 12 is optically coupled at one end thereof with the light source 11, and guides the light L1 emitted from the light source 11. For example, a light guide or an optical fiber is suitably used as the light guiding member 12. The light emitting part 13 is optically coupled with the other end of the light guiding member 12, and emits the light L1 guided by the light guiding member 12 onto the measurement object 100. The light emitting part 13 is placed in a position facing the first film 102 of the measurement object 100, that is, in a position facing the front surface 101a of the base material 101.

The light detection unit 20A detects the wavelength-dependent intensity (spectrum) of light reflected on the front surface 101a side of the measurement object 100. The light detection unit 20A includes a light incident part 21a, a light guiding member 22a, and a spectroscopic detection unit 23a. Reflected light L2 from the measurement object 100 enters the light incident part 21a. The light incident part 21a is placed in a position facing the first film 102 of the measurement object 100, that is, in a position facing the front surface 101a of the base material 101. The optical axis of the light emitting part 13 and the optical axis of the light incident part 21a may be parallel to each other, or may intersect each other at the measurement object 100. The optical axes of the light emitting part 13 and the optical axis of the light incident part 21a may coincide with each other. The light guiding member 22a is optically coupled at one end thereof with the light incident part 21a, and guides the reflected light L2 incident to the light incident part 21a. For example, a light guide or an optical fiber is suitably used as the light guiding member 22a. The spectroscopic detection unit 23a is optically coupled with the other end of the light guiding member 22a. The spectroscopic detection unit 23a spectrally separates the reflected light L2 guided by the light guiding member 22a into wavelength components, and detects the wavelength-dependent intensity of the spectrally separated light. The spectroscopic detection unit 23a is suitably configured by combining, for example, a spectroscopic optical element (such as a prism or a grating element) with an image pickup device (such as a line sensor, an area image sensor, a photomultiplier tube, or a photodiode). The spectroscopic detection unit 23a outputs the detected light intensity as an electric signal.

The film thickness calculation unit 30A obtains the film thicknesses of the first and second films 102 and 103 based on the detection result in the light detection unit 20A. In other words, the film thickness calculation unit 30A obtains the film thicknesses of the first and second films 102 and 103 by comparing measured spectral reflectance that is wavelength-dependent reflectance obtained based on the detection result in the light detection unit 20A with theoretical spectral reflectance that is wavelength-dependent theoretical reflectance, and by fitting the measured and theoretical reflectance values to each other.

The film thickness measurement device 1A further includes a control unit 40, a display unit 50, and an input device 60, in addition to the configuration described above.

The control unit 40 is a unit to control operations of the light emission unit 10, the light detection unit 20A, and the film thickness calculation unit 30A, and is suitably implemented by, for example, a computer having a CPU and a memory. The display unit 50 displays values of the film thicknesses of the first and second films 102 and 103 calculated by the film thickness calculation unit 30A, and also displays, for example, measurement conditions. The input device 60 is constituted by, for example, a mouse and/or a keyboard, and is used when an operator enters, for example, the measurement conditions. The display unit 50 and the input device 60 may be integrated as a touchscreen panel display. The control unit 40, the display unit 50, and the input device 60 may be provided outside the film thickness measurement device 1A.

Figure 3:
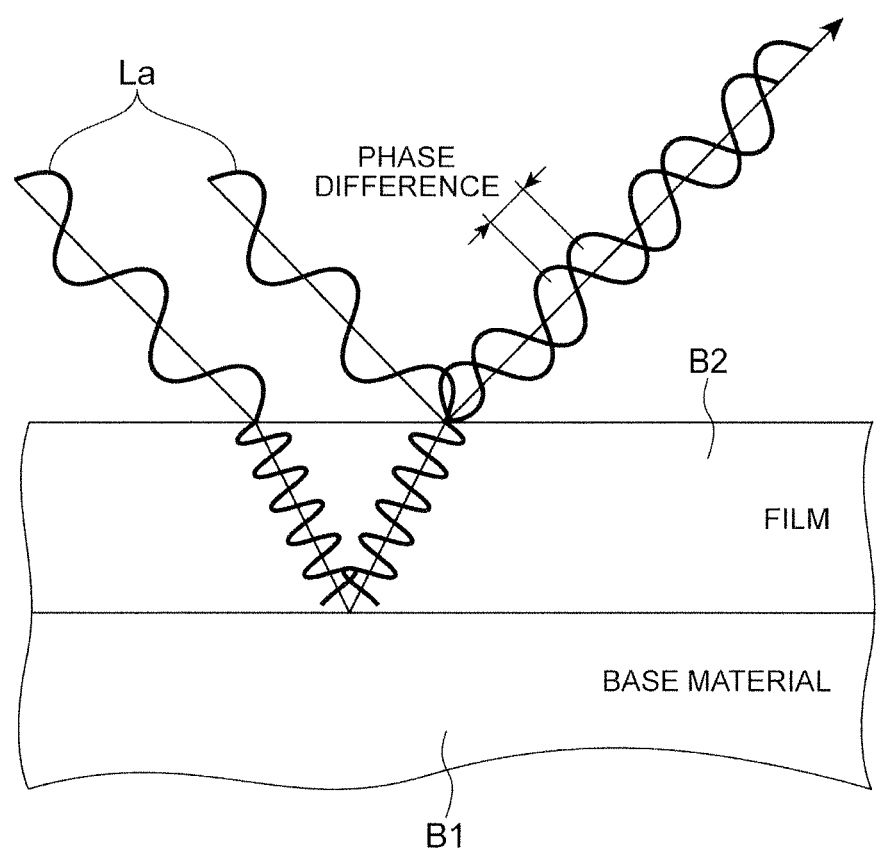
FIG. 3 is a diagram for explaining the principle of film thickness measurement, and shows a section of a film formed on a base material.

The film thickness measurement method using the film thickness measurement device 1A of the present embodiment will be described in detail. FIG. 3 is a diagram for explaining the principle of the film thickness measurement, and shows a section of a film B2 formed on a base material B1. When incoherent light La enters the film B2, light reflected on a surface of the film B2 and light reflected on the interface between the base material B1 and the film B2 interfere with each other. The light path length of the light reflected on the interface between the base material B1 and the film B2 is larger than the light path length of the light reflected on the surface of the film B2 by the length of a light path in the film B2, so that a phase difference corresponding to the thickness of the film B2 is produced between these beams of reflected light.

Figure 4:
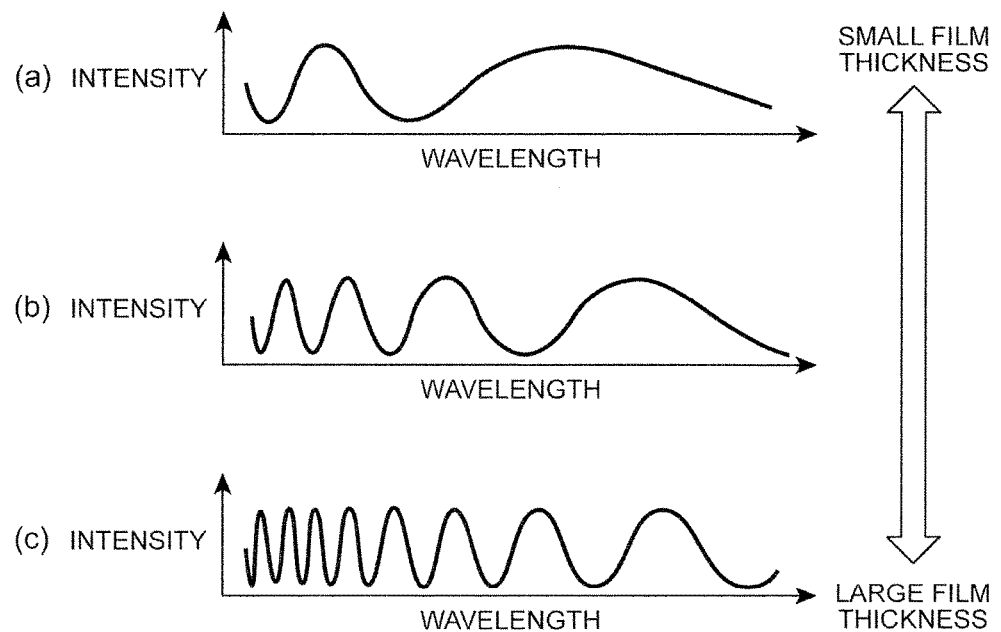
FIG. 4 shows graphs each showing a relation between the intensity and the wavelength of reflected light after interference.

FIGS. 4(a) to 4(c) are graphs each showing a relation between the intensity and the wavelength of the reflected light after the interference. FIG. 4(a) shows a case in which the film thickness of the film B2 is smaller than those in the other cases. FIG. 4(c) shows a case in which the film thickness of the film B2 is larger than those in the other cases. As shown in FIG. 4, the spectrum (reflected spectrum) of the reflected light after the interference undulates due to the interference, and intervals of the undulation decrease as the film thickness of the film B2 increases.

Figure 5:
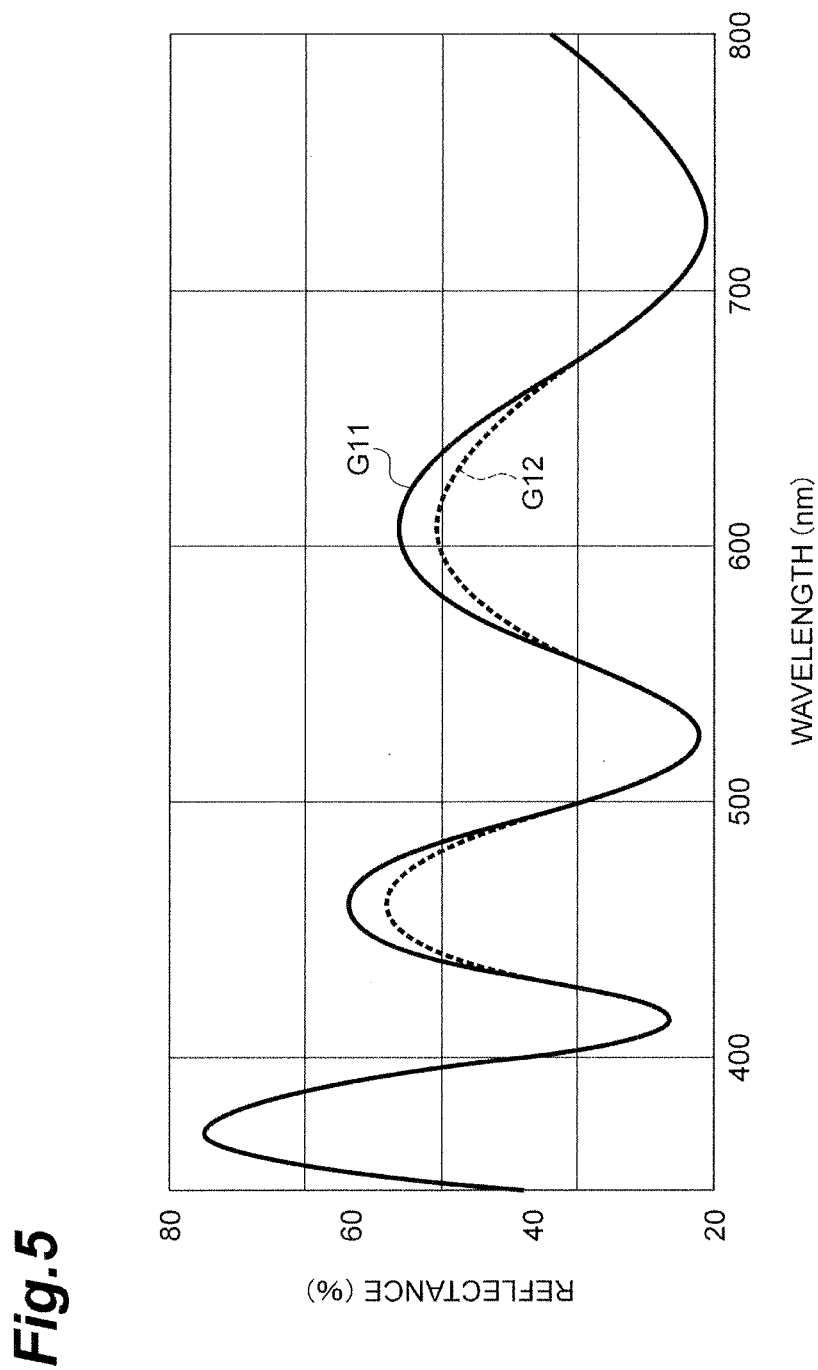
FIG. 5 is a graph showing an example of curve fitting when the film is an ITO film.

The film thickness of the film B2 can be obtained using the relation between the reflected spectrum and the film thickness of the film B2 obtained as described above. A fast Fourier transformation method or a curve-fitting method serves as a specific method. The fast Fourier transformation method is a method in which the fast Fourier transformation is applied to the reflected spectrum, and the film thickness is obtained from the peak frequency of the Fourier transform. The curve-fitting method is a method in which the spectral reflectance values (measured spectral reflectance values) obtained from the measured reflected spectrum are fitted to the theoretical spectral reflectance calculated from a theoretical formula, and the film thickness is obtained from the theoretical spectral reflectance thus fitted. The present embodiment uses the curve-fitting method. According to the curve-fitting method, the thickness of the film B2 can be accurately measured even if the thickness is 1 μm or smaller. FIG. 5 is a graph showing an example of the curve fitting when the film B2 is an ITO film (with a thickness of 350 nm). In FIG. 5, graph G11 shows the measured spectral reflectance, and graph G12 shows the theoretical spectral reflectance. For example, the film thickness value obtained by the theoretical spectral reflectance minimizing the square of the difference between graphs G11 and G12 is determined to be the thickness of the film B2.

However, in the measurement object 100 of the present embodiment, the films 102 and 103 are formed on both surfaces of the base material 101 as shown in FIG. 1, so that the reflected spectrum after the interference by the second film 103 is superimposed on the reflected spectrum after the interference by the first film 102. Accordingly, when the film thickness of the first film 102 is intended to be measured by directly applying the method described above, an accurate value is difficult to be obtained.

Hence, in order to reflect the influence of the multiple reflection in the base material 101, the theoretical spectral reflectance according to the present embodiment takes into account the reflectance on the front surface 101a of the base material 101 (front surface reflectance) that depends on the refractive index and the film thickness of the first film 102, the transmissivity through the front surface 101a of the base material 101 (front surface transmissivity) that also depends on the refractive index and the film thickness of the first film 102, and the reflectance on the back surface 101b of the base material 101 (back surface reflectance). The reflectance on the back surface 101b of the base material 101 includes the influence of light reflected on the back surface 101b, and also includes the influence of light that passes through the back surface 101b, is reflected on the boundary between the second film 103 and the periphery (air or vacuum), and returns to the base material 101 among the irradiated light L1 passing through the inside of the base material 101. Therefore, the reflectance on the back surface 101b of the base material 101 depends on the refractive index and the film thickness of the second film 103.

Figure 6:
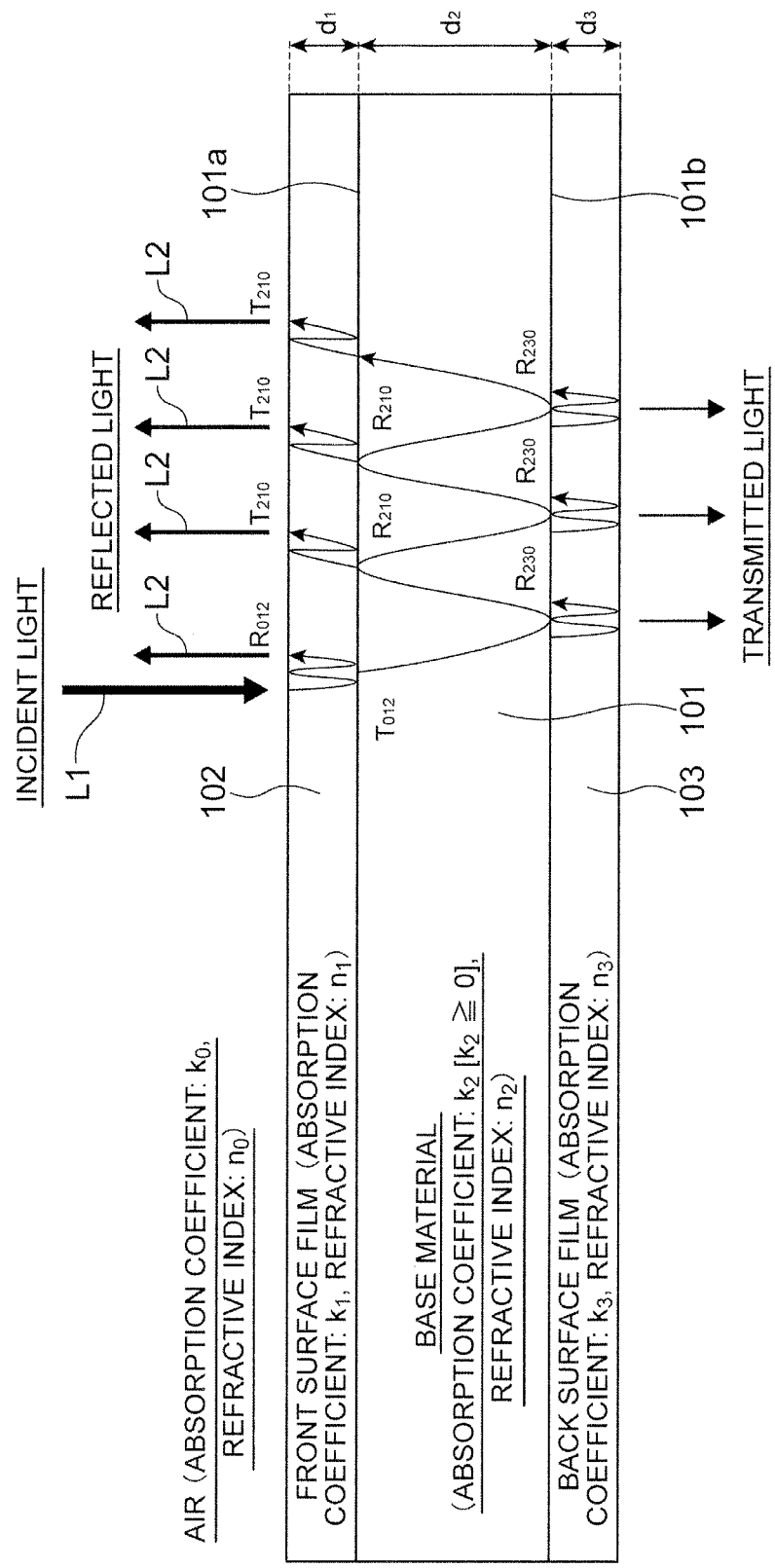
FIG. 6 is a diagram showing definitions of parameters contained in Expressions (1) to (3).

Expressions (1) and (2) are expressions representing theoretical spectral reflectance $R_{theory}$ according to the present embodiment. The symbol $\lambda$ represents a wavelength. FIG. 6 is a diagram showing definitions of parameters contained in Expressions (1) to (3). As shown in FIG. 6, in Expressions (1) and (2), $k_0$ denotes the extinction coefficient of the periphery (air or vacuum) of the measurement object 100; $k_1$ denotes the extinction coefficient of the first film 102; $k_2$ denotes the extinction coefficient of the base material 101 (where $k_2 \geq 0$); and $k_3$ denotes the extinction coefficient of the second film 103. Also, $n_0$ denotes the refractive index of the periphery (air or vacuum) of the measurement object 100; $n_1$ denotes the refractive index of the first film 102; $n_2$ denotes the refractive index of the base material 101; and $n_3$ denotes the refractive index of the second film 103. Also, $R_{012}(\lambda)$ denotes the reflectance (first front surface reflectance) on the front surface 101a on the side of the first film 102; $R_{230}(\lambda)$ denotes the reflectance (back surface reflectance) on the back surface 101b on the side of the base material 101; and $R_{210}(\lambda)$ denotes the reflectance (second front surface reflectance) on the front surface 101a on the side of the base material 101. Also, $T_{012}(\lambda)$ denotes the transmissivity (front surface transmissivity) through the front surface 101a on the side of the first film 102; and $T_{210}(\lambda)$ denotes the transmissivity through the surface of the first film 102 on the side of the first film 102. Moreover, $d_1$ denotes the film thickness of the first film 102; $d_2$ denotes the thickness of the base material 101; and $d_3$ denotes the film thickness of the second film 103.

Expression (1)

$$R_{theory} = R_{012}(\lambda) + T_{012}(\lambda)T_{210}(\lambda)R_{230}(\lambda)\exp(-4A_2)\sum_{n=0}^{\infty}[R_{230}(\lambda)R_{210}(\lambda)\exp(-4A_2)]^n \qquad (1)$$

Expression (2)

$$A_2 = \frac{2\pi}{\lambda} k_2 d_2 \qquad (2)$$

As shown in Expressions (1) and (2), in order to reflect the first front surface reflectance $R_{012}(\lambda)$ being the reflectance on the front surface 101a of the base material 101 on the side of the first film 102 and also to reflect the influence of the multiple reflection in the base material 101, theoretical spectral reflectance $R_{theory}$ takes into account the second front surface reflectance $R_{210}(\lambda)$ being the reflectance on the front surface 101a on the side of the base material 101, the front surface transmissivity $T_{012}(\lambda)$ being the transmissivity through the front surface 101a, and the reflectance (back surface reflectance) $R_{230}(\lambda)$ on the back surface 101b on the side of the base material 101. Specifically, the Σ term on the right-hand side of Expression (1) represents the multiple reflection component in the base material 101, and the multiple reflection component is based on the reflectance $R_{230}(\lambda)$ on the back surface 101b as viewed from the side of the base material 101, the reflectance $R_{210}(\lambda)$ on the front surface 101a as viewed from the side of the base material 101, and the transmissivity $T_{012}(\lambda)$ through the front surface 101a.

Figure 7:
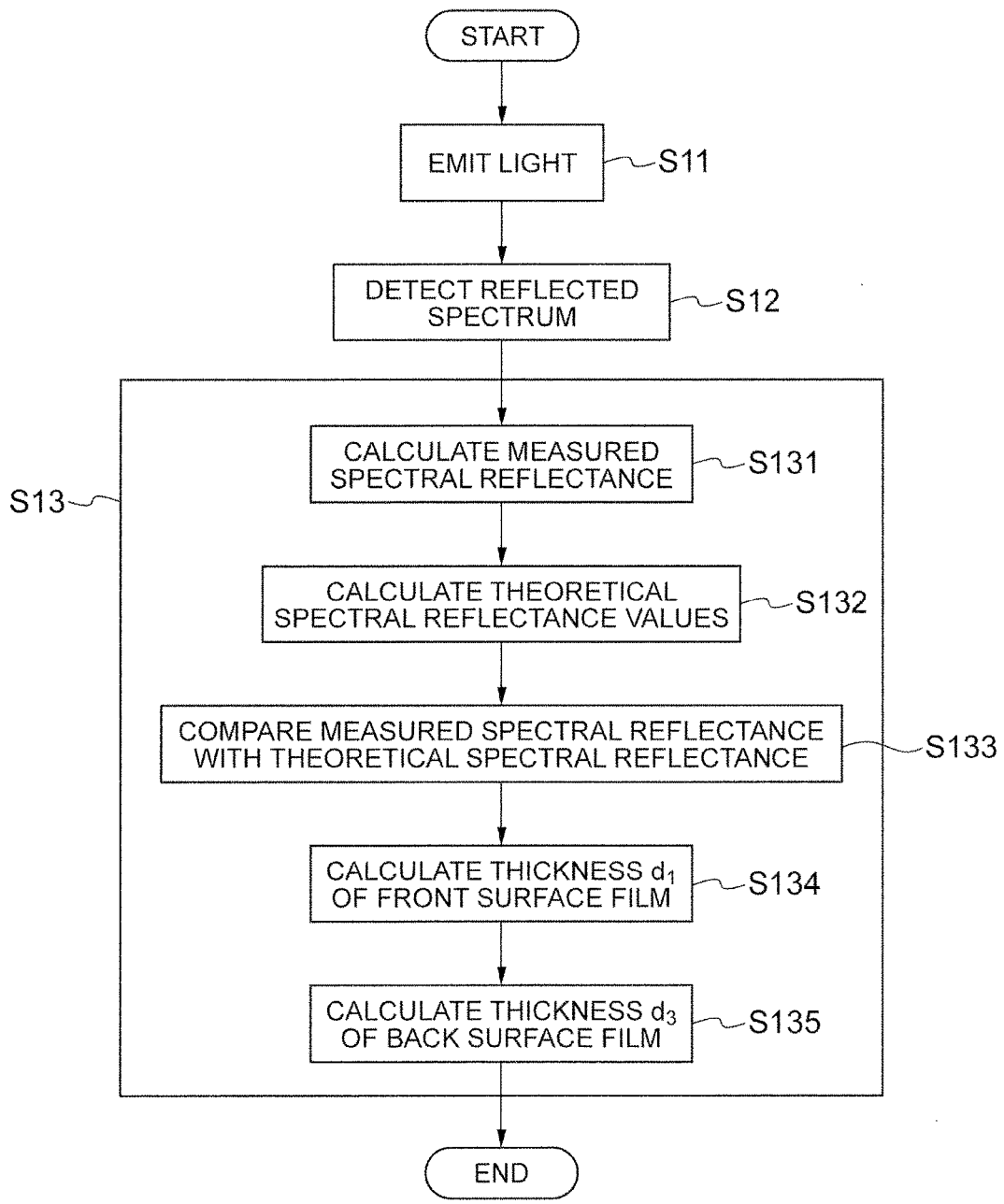
FIG. 7 is a flowchart showing the operation of the film thickness measurement device and the film thickness measurement method according to the first embodiment.

FIG. 7 is a flowchart showing the operation and the film thickness measurement method of the film thickness measurement device 1A according to the present embodiment. As shown in FIG. 7, the light emission unit 10 first emits the incoherent light L1, such as white light, onto the front surface 101a side of the measurement object 100 (light emitting step S11). Then, the light detection unit 20A spectrally separates the reflected light L2 on the front surface 101a side of the measurement object 100 into the wavelength components, and detects the intensity of each of the wavelength components (light detecting step S12).

Subsequently, the film thickness calculation unit 30A obtains the film thicknesses of the first and second films 102 and 103 (film thickness identifying step S13). At this film thickness identifying step S13, the film thickness calculation unit 30A first calculates the measured spectral reflectance based on the detection signals from the light detection unit 20A (step S131). For this purpose, the film thickness calculation unit 30A first obtains a reflected spectrum $S_{sig}(\lambda)$ from the wavelength-dependent intensity of the reflected light L2. The film thickness calculation unit 30A then calculates a ratio between a reference reflected spectrum $S_{ref}(\lambda)$ obtained in advance using a reference measurement object and the reflected spectrum $S_{sig}(\lambda)$, as shown in Expression (3). This ratio is measured spectral reflectance $R_{sig}(\lambda)$.

Expression (3)

$$R_{sig}(\lambda) = \frac{S_{sig}(\lambda)}{S_{ref}(\lambda)} \qquad (3)$$

The film thickness calculation unit 30A subsequently calculates the theoretical spectral reflectance $R_{theory}$ (step S132). First, the operator enters the extinction coefficient $k_2$, the refractive index $n_2$, and the thickness $d_2$ of the base material 101; the extinction coefficient $k_1$ and the refractive index $n_1$ of the first film 102; and the extinction coefficient $k_3$ and the refractive index $n_3$ of the second film 103. The film thickness calculation unit 30A changes each of the values of the first front surface reflectance $R_{012}(\lambda)$, the second front surface reflectance $R_{210}(\lambda)$, the front surface transmissivity $T_{012}(\lambda)$, the transmissivity $T_{210}(\lambda)$, and the back surface reflectance $R_{230}(\lambda)$ that appear in Expression (1), and thus obtains a plurality of values of the theoretical spectral reflectance $R_{theory}$ constituted by a combination of a plurality of values of the first front surface reflectance $R_{012}(\lambda)$, a plurality of values of the second front surface reflectance $R_{210}(\lambda)$, a plurality of values of the front surface transmissivity $T_{012}(\lambda)$, a plurality of values of the transmissivity $T_{210}(\lambda)$, and a plurality of values of the back surface reflectance $R_{230}(\lambda)$.

The film thickness calculation unit 30A subsequently compares the values of the theoretical spectral reflectance $R_{theory}$ with the measured spectral reflectance $R_{sig}(\lambda)$, and obtains the theoretical spectral reflectance $R_{theory}$ closest (most fitted) to the measured spectral reflectance $R_{sig}(\lambda)$ (step S133). For example, the least squares method is used at this step S133. Specifically, the film thickness calculation unit 30A obtains the value of the square of the difference between the measured spectral reflectance $R_{sig}(\kappa)$ and the theoretical spectral reflectance $R_{theory}$ for each of the values of the theoretical spectral reflectance $R_{theory}$, and selects the theoretical spectral reflectance $R_{theory}$ that minimizes the value of the square.

The film thickness calculation unit 30A subsequently calculates the film thickness $d_1$ of the first film 102 based on the theoretical spectral reflectance $R_{theory}$ closest (substantially equal) to the measured spectral reflectance $R_{sig}(\lambda)$ (step S134). As shown in Expressions (4) to (6) given below, theoretical first front surface reflectance $R_{theory012}(\lambda)$ depends on the refractive index and the film thickness of the first film 102, and is a function of the film thickness $d_1$. In Expressions (4) to (6), $r_{01}$ denotes the amplitude reflection coefficient on the interface between air and the first film 102, and $r_{12}$ denotes the amplitude reflection coefficient on the interface between the first film 102 and the base material 101, where $N_1 = n_1 - ik_1$.

Expression (4)

$$R_{theory012} = |r_{012}|^2 \qquad (4)$$

Expression (5)

$$r_{012} = \frac{r_{01} + r_{12}e^{-2i\delta_1}}{1 + r_{01}r_{12}e^{-2i\delta_1}} \qquad (5)$$

Expression (6)

$$\delta_1 = \frac{2\pi}{\lambda} N_1 d_1 \qquad (6)$$

As shown in Expressions (7) to (9) given below, theoretical second front surface reflectance $R_{theory210}(\lambda)$ depends on the refractive index and the film thickness of the first film 102, and is a function of the film thickness $d_1$. In Expressions (7) to (9), $r_{21}$ denotes the amplitude reflection coefficient on the interface between the base material and the first film 102, and $r_{10}$ denotes the amplitude reflection coefficient on the interface between the first film 102 and air.

Expression (7)

$$R_{theory210} = |r_{210}|^2 \quad (7)$$

Expression (8)

$$r_{210} = \frac{r_{21} + r_{10}e^{-2i\delta_1}}{1 + r_{21}r_{10}e^{-2i\delta_1}} \quad (8)$$

Expression (9)

$$\delta_1 = \frac{2\pi}{\lambda} N_1 d_1 \quad (9)$$

In addition, as shown in Expressions (10) to (12) given below, theoretical front surface transmissivity $T_{theory012}(\lambda)$ also depends on the refractive index and the film thickness of the first film 102, and is a function of the film thickness $d_1$. In Expressions (10) to (12), $t_{01}$ denotes the amplitude transmission coefficient on the interface between air and the first film 102, and $t_{12}$ denotes the amplitude transmission coefficient on the interface between the first film 102 and the base material, where $N_2 = n_2 - ik_2$.

Expression (10)

$$T_{theory012} = \text{Re}\left[\frac{N_2}{N_0}\right]|t_{012}|^2 \quad (10)$$

Expression (11)

$$t_{012} = \frac{t_{01}t_{12}e^{-i\delta_1}}{1 + r_{01}r_{12}e^{-2i\delta_1}} \quad (11)$$

Expression (12)

$$\delta = \frac{2\pi}{\lambda} N_1 d_1 \quad (12)$$

Moreover, as shown in Expressions (13) to (15) given below, theoretical transmissivity $T_{theory210}(\lambda)$ through the surface of the first film 102 also depends on the refractive index and the film thickness of the first film 102, and is a function of the film thickness $d_1$. In Expressions (13) to (15), $t_{21}$ denotes the amplitude transmission coefficient on the interface between the base material and the first film 102, and $t_{10}$ denotes the amplitude transmission coefficient on the interface between the first film 102 and air.

Expression (13)

$$T_{theory210} = \text{Re}\left[\frac{N_0}{N_2}\right]|t_{210}|^2 \quad (13)$$

Expression (14)

$$t_{210} = \frac{t_{21}t_{10}e^{-i\delta_1}}{1 + r_{21}r_{10}e^{-2i\delta_1}} \quad (14)$$

Expression (15)

$$\delta = \frac{2\pi}{\lambda} N_1 d_1 \quad (15)$$

Accordingly, the film thickness calculation unit 30A obtains the value of the film thickness $d_1$ from each of the first front surface reflectance $R_{012}(\lambda)$, the second front surface reflectance $R_{210}(\lambda)$, the front surface transmissivity $T_{012}(\lambda)$, and the transmissivity $T_{210}(\lambda)$ for the theoretical spectral reflectance $R_{theory}$ selected at step S133. The film thickness calculation unit 30A then determines and outputs the mean value or the least-square-estimated value from the values of the film thickness $d_1$ thus obtained as the film thickness of the first film 102 of the measurement object 100. Any one of the obtained values of the film thickness $d_1$ may be determined to be the film thickness of the first film 102 of the measurement object 100. Since the reflectance $R_{012}(\lambda)$ on the front surface 101a on the side of the first film 102 has a particularly large influence, the value of the film thickness $d_1$ obtained from the first front surface reflectance $R_{012}(\lambda)$ for the theoretical spectral reflectance $R_{theory}$ may be determined to be the film thickness of the first film 102.

The film thickness calculation unit 30A also calculates the film thickness $d_3$ of the second film 103 (step S135). As shown in Expressions (16) to (18), theoretical back surface reflectance $R_{theory230}(\lambda)$ depends on the refractive index and the film thickness of the second film 103, and is a function of the film thickness $d_3$. In Expressions (16) to (18), $r_{23}$ denotes the amplitude reflection coefficient on the interface between the base material 101 and the second film 103, and $r_{30}$ denotes the amplitude reflection coefficient on the interface between the second film 103 and air, where $N_3 = n_3 - ik_3$.

Expression (16)

$$R_{theory230} = |r_{230}|^2 \quad (16)$$

Expression (17)

$$r_{230} = \frac{r_{23} + r_{30}e^{-2i\delta_3}}{1 + r_{23}r_{30}e^{-2i\delta_3}} \quad (17)$$

Expression (18)

$$\delta_3 = \frac{2\pi}{\lambda} N_3 d_3 \quad (18)$$

Based on Expressions (16) to (18), the film thickness calculation unit 30A obtains the value of the film thickness $d_3$ from the reflectance $R_{theory230}(\lambda)$ that fits to the back surface reflectance $R_{230}(\lambda)$ for the theoretical spectral reflectance $R_{theory}$ selected at step S133, and determines and outputs the value thus obtained as the film thickness of the second film 103 of the measurement object 100.

As described above, at the film thickness identifying step S13 of the present embodiment, the film thickness calculation unit 30A obtains the film thickness $d_1$ of the first film 102 and the film thickness $d_3$ of the second film 103 by comparing the measured spectral reflectance $R_{sig}(\lambda)$ obtained based on the detection result at the light detecting step S12 with the theoretical spectral reflectance $R_{theory}$ that takes into account the first front surface reflectance $R_{012}(\lambda)$ and the second front surface reflectance $R_{210}(\lambda)$ that are the reflectance on the side of the front surface 101a, the front surface transmissivity $T_{012}(\lambda)$ and the transmissivity $T_{210}(\lambda)$ that are the transmissivity on the side of the front surface 101a, and the back surface reflectance $R_{230}(\lambda)$ that is the reflectance on the side of the back surface 101b. The process at step S134 for calculating the film thickness $d_1$ of the first film 102 and the process at step S135 for calculating the film thickness $d_3$ of the second film 103 can be performed in any order. The process at step S135 may be performed first, or the processes at steps S134 and S135 may be performed in parallel.

Figure 8:
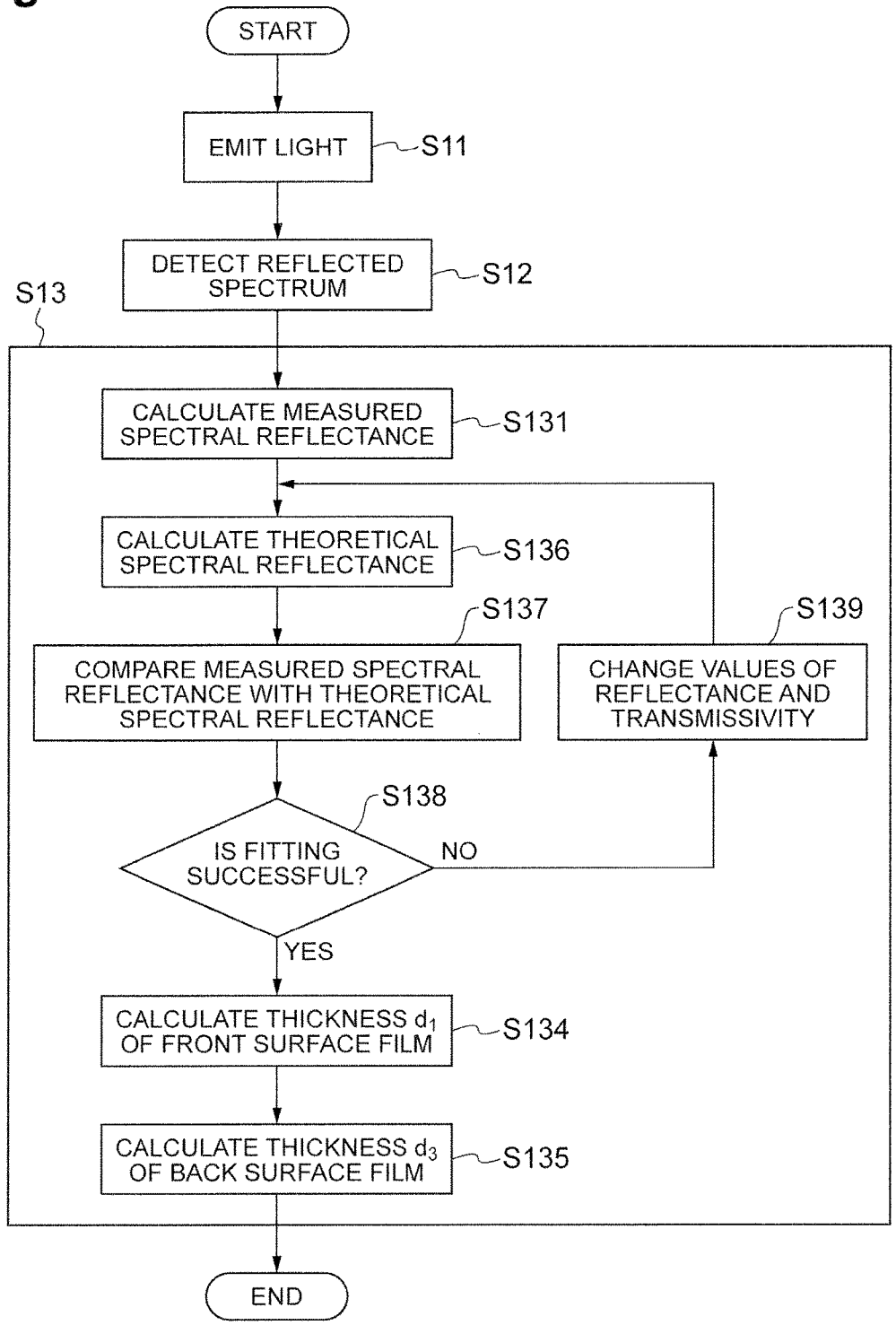
FIG. 8 is a flowchart showing another example of the operation of the film thickness measurement device and the film thickness measurement method according to the first embodiment.

In the present embodiment, the example has been shown in which the values of the theoretical spectral reflectance $R_{theory}$ are calculated in advance, and the measured spectral reflectance $R_{sig}(\lambda)$ is tried to be fitted to each of the values of the theoretical spectral reflectance $R_{theory}$. However, the fitting between the theoretical spectral reflectance $R_{theory}$ and the measured spectral reflectance $R_{sig}(\lambda)$ is not limited to such a form of fitting. For example, the fitting may be performed in the following manner. Specifically, as shown in FIG. 8, a value of the theoretical spectral reflectance $R_{theory}$ is calculated that is constituted by a combination of a value of the first front surface reflectance $R_{012}(\lambda)$, a value of the second front surface reflectance $R_{210}(\lambda)$, a value of the front surface transmissivity $T_{012}(\lambda)$, a value of the transmissivity $T_{210}(\lambda)$, and a value of the back surface reflectance $R_{230}(\lambda)$ (step S136). This value of the theoretical spectral reflectance $R_{theory}$ is tried to be fitted to the measured spectral reflectance $R_{sig}(\lambda)$ (step S137). If the fitting is not successful (the square of the difference exceeds a threshold) (No at step S138), the combination of the values of the first front surface reflectance $R_{012}(\lambda)$, the second front surface reflectance $R_{210}(\lambda)$, the front surface transmissivity $T_{012}(\lambda)$, the transmissivity $T_{210}(\lambda)$, and the back surface reflectance $R_{230}(\lambda)$ is changed (step S139), and the changed value of the theoretical spectral reflectance $R_{theory}$ is tried again to be fitted to the measured spectral reflectance $R_{sig}(\lambda)$. By repeating the processing described above, a value of the theoretical spectral reflectance $R_{theory}$ among a plurality of values of the theoretical spectral reflectance $R_{theory}$ can be obtained that fits to the measured spectral reflectance $R_{sig}(\lambda)$.

Figure 9:
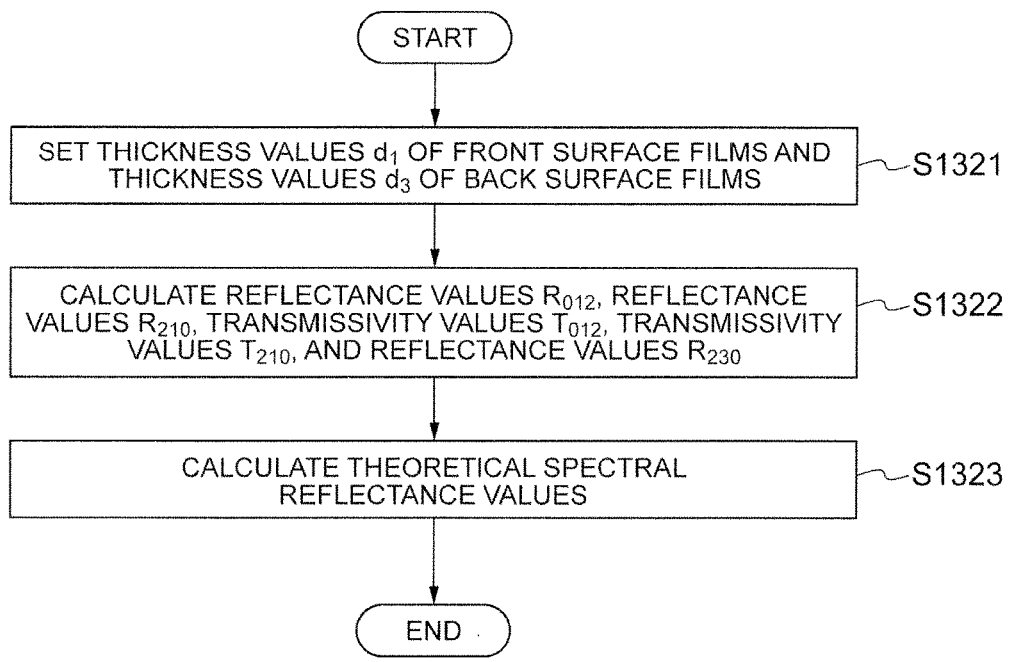
FIG. 9 is a flowchart showing a method for calculating a plurality of theoretical spectral reflectance values.

In the present embodiment, the example has been shown in which the film thickness $d_1$ of the first film 102 and the film thickness $d_3$ of the second film 103 are obtained from the value of the first front surface reflectance $R_{012}(\lambda)$ the value of the second front surface reflectance $R_{210}(\lambda)$, the value of the front surface transmissivity $T_{012}(\lambda)$, the value of the transmissivity $T_{210}(\lambda)$, and the value of the back surface reflectance $R_{230}(\lambda)$ for the theoretical spectral reflectance $R_{theory}(\lambda)$ closest to the measured spectral reflectance $R_{sig}(\lambda)$. However, the theoretical spectral reflectance $R_{theory}$ may be prepared by changing the value of the film thickness $d_1$ of the first film 102 in Expressions (6), (9), (12), and (15) and the value of the film thickness $d_3$ of the second film 103 in Expression (18). Specifically, first, at step S132 for calculating the values of the theoretical spectral reflectance shown in FIG. 7, a plurality of values of the film thickness $d_1$ of the first film 102 and a plurality of values of the film thickness $d_3$ of the second film 103 are set (S1321), as shown in FIG. 9. Then, for the values of the film thickness $d_1$ and the film thickness $d_3$ thus set, a plurality of values of the first front surface reflectance $R_{012}(\lambda)$, a plurality of values of the second front surface reflectance $R_{210}(\lambda)$ a plurality of values of the front surface transmissivity $T_{012}(\lambda)$, a plurality of values of the transmissivity $T_{210}(\lambda)$ and a plurality of values of the back surface reflectance $R_{230}(\lambda)$ are calculated (S1322). Then, a plurality of values of the theoretical spectral reflectance $R_{theory}$ are calculated that correspond to the values of the first front surface reflectance $R_{012}(\lambda)$, the values of the second front surface reflectance $R_{210}(\lambda)$, the values of the front surface transmissivity $T_{012}(\lambda)$, the values of the transmissivity $T_{210}(\lambda)$, and the values of the back surface reflectance $R_{230}(\lambda)$ that have been calculated (S1323). Alternatively, at step S139 for changing the reflectance and the transmissivity shown in FIG. 7, each value of the reflectance and the transmissivity may be changed by changing the value of the film thickness $d_1$ of the first film 102 and the value of the film thickness $d_3$ of the second film 103. In these cases, the theoretical spectral reflectance $R_{theory}(\lambda)$ corresponding to a value of the film thickness $d_1$ and a value of the film thickness $d_3$ can be compared with the measured spectral reflectance $R_{sig}(\lambda)$, so that the value of the film thickness $d_1$ and the value of the film thickness $d_3$ can be determined by obtaining the theoretical spectral reflectance $R_{theory}(\lambda)$ closest to the measured spectral reflectance $R_{sig}(\lambda)$ without performing the process at step S134 for calculating the film thickness $d_1$ of the front surface film and the process at step S135 for calculating the film thickness $d_3$ of the back surface film.

The following describes advantageous effects obtained by the film thickness measurement device 1A and the film thickness measurement method according to the present embodiment described above. As described above, when the thin films are formed on both the front and back surfaces of the base material, the light reflected from the back surface of the base material has an influence on the measurement of the thickness of the thin film on the front surface. The degree of this influence depends on the reflectance on the back surface side of the base material, and the reflectance on the back surface side of the base material changes with the refractive index and the thickness of the thin film formed on the back surface. To solve this problem, at the film thickness identifying step S13 in the present embodiment, the film thickness calculation unit 30A compares (fits) the theoretical spectral reflectance $R_{theory}$ that takes into account the second front surface reflectance $R_{210}(\lambda)$ on the front surface 101a on the side of the base material 101, the transmissivity $T_{012}(\lambda)$ through the front surface 101a, and the back surface reflectance $R_{230}(\lambda)$ on the back surface 101b on the side of the base material 101 with the measured spectral reflectance $R_{sig}(\lambda)$. The film thickness calculation unit 30A then determines the film thickness $d_1$ of the first film 102 based on a value of the theoretical spectral reflectance $R_{theory}$ closest to the measured spectral reflectance $R_{sig}(\lambda)$ among the values of the theoretical spectral reflectance $R_{theory}$ obtained by changing the second front surface reflectance $R_{210}(\lambda)$ on the front surface 101a on the side of the base material 101, the transmissivity $T_{012}(\lambda)$ through the front surface 101a, and the back surface reflectance $R_{230}(\lambda)$ on the back surface 101b on the side of the base material 101. As a result, the influence of the multiple reflection in the base material 101 can be reflected in the theoretical spectral reflectance $R_{theory}$, so that the film thickness $d_1$ of the first film 102 on the front surface 101a can be accurately measured. Moreover, the theoretical spectral reflectance $R_{theory}$ is compared (fitted) with the measured spectral reflectance $R_{sig}(\lambda)$, the theoretical spectral reflectance $R_{theory}$ taking into account the first front surface reflectance $R_{012}(\lambda)$ and the second front surface reflectance $R_{210}(\lambda)$ as the reflectance on the side of the front surface 101a, the front surface transmissivity $T_{012}(\lambda)$ and the transmissivity $T_{210}(\lambda)$ on the surface of the first film 102 as the transmissivity on the side of the front surface 101a, and the back surface reflectance $R_{230}(\lambda)$ as the reflectance on the side of the back surface 101b. Then, the film thickness $d_1$ of the first film 102 is determined based on at least one of the first front surface reflectance $R_{012}(\lambda)$, the second front surface reflectance $R_{210}(\lambda)$, the front surface transmissivity $T_{012}(\lambda)$, and the transmissivity $T_{210}(\lambda)$ for the value of the theoretical spectral reflectance $R_{theory}$ closest to the measured spectral reflectance $R_{sig}(\lambda)$ among the values of the theoretical spectral reflectance $R_{theory}$ obtained by changing each of the first front surface reflectance $R_{012}(\lambda)$ on the side of the front surface 101a, the second front surface reflectance $R_{210}(\lambda)$, the front surface transmissivity $T_{012}(\lambda)$, the transmissivity $T_{210}(\lambda)$ through the surface of the first film 102, and the back surface reflectance $R_{230}(\lambda)$ on the side of the back surface 101b. Thus, the accuracy of measurement of the film thickness $d_1$ of the first film 102 on the front surface 101a can be further improved.

As performed in the present embodiment, the values of the theoretical spectral reflectance $R_{theory}$ may be obtained by calculating the first front surface reflectance $R_{012}(\lambda)$ on the side of the front surface 101a, the second front surface reflectance $R_{210}(\lambda)$, the front surface transmissivity $T_{012}(\lambda)$, the transmissivity $T_{210}(\lambda)$ through the surface of the first film 102, and the back surface reflectance $R_{230}(\lambda)$ on the side of the back surface 101b for the value of the film thickness of the first film 102 and the value of the film thickness of the second film 103, and by changing the value of the film thickness of the first film 102 and the value of the film thickness of the second film 103. As a result, the values of the theoretical spectral reflectance $R_{theory}$ can be suitably obtained.

As performed in the present embodiment, the value of the film thickness of the first film 102 may be obtained based on at least either pair of the front surface reflectance values $R_{012}(\lambda)$ and $R_{210}(\lambda)$ and the front surface transmissivity values $T_{012}(\lambda)$ and $T_{210}(\lambda)$ for the value of the theoretical spectral reflectance $R_{theory}$ closest to the measured spectral reflectance $R_{sig}(\lambda)$. As a result, the film thickness of the first film 102 can be suitably obtained.

As performed in the present embodiment, the film thickness $d_3$ of the second film 103 may be determined based on the value of the theoretical spectral reflectance $R_{theory}$ closest to the measured spectral reflectance $R_{sig}(\lambda)$. As a result, both the film thickness $d_1$ of the first film 102 on the front surface 101a and the film thickness $d_3$ of the second film 103 on the back surface 101b can be accurately measured by one measurement operation. The film thickness identifying step S13 or the film thickness calculation unit 30A of the present embodiment determines the film thickness $d_1$ of the first film 102 and the film thickness $d_3$ of the second film 103, but may determine only the film thickness $d_1$ of the first film 102.

As performed in the present embodiment, the value of the film thickness of the second film 103 may be obtained by calculation based on a value of the back surface reflectance $R_{230}(\lambda)$ for the value of the theoretical spectral reflectance $R_{theory}$ closest to the measured spectral reflectance $R_{sig}(\lambda)$. As a result, the value of the film thickness of the second film 103 can be suitably obtained.

In the present embodiment, the measured spectral reflectance $R_{sig}(\lambda)$ and the theoretical spectral reflectance $R_{theory}$ are directly fitted to each other. However, for example, each of the measured spectral reflectance $R_{sig}(\lambda)$ and the theoretical spectral reflectance $R_{theory}$ may be Fourier transformed, and the frequency distribution of the measured spectral reflectance $R_{sig}(\lambda)$ and the frequency distribution of the theoretical spectral reflectance $R_{theory}$ may be fitted to each other.

First Modification

The first embodiment has exemplified the case in which each of the first and second films 102 and 103 consists of one layer. However, when either one or both of the first and second films 102 and 103 includes or each include a plurality of layers, the layer thickness of each of the layers can also be obtained. A first modification of the present invention uses a theoretical spectral reflectance value that takes into account the reflectance (first front surface reflectance) on the side of the front surface 101a that depends on the refractive indices and the layer thicknesses of the layers included in the first film 102 and the reflectance (back surface reflectance) on the side of the back surface 101b that depends on the refractive indices and the layer thicknesses of the layers included in the second film 103.

Figure 10:
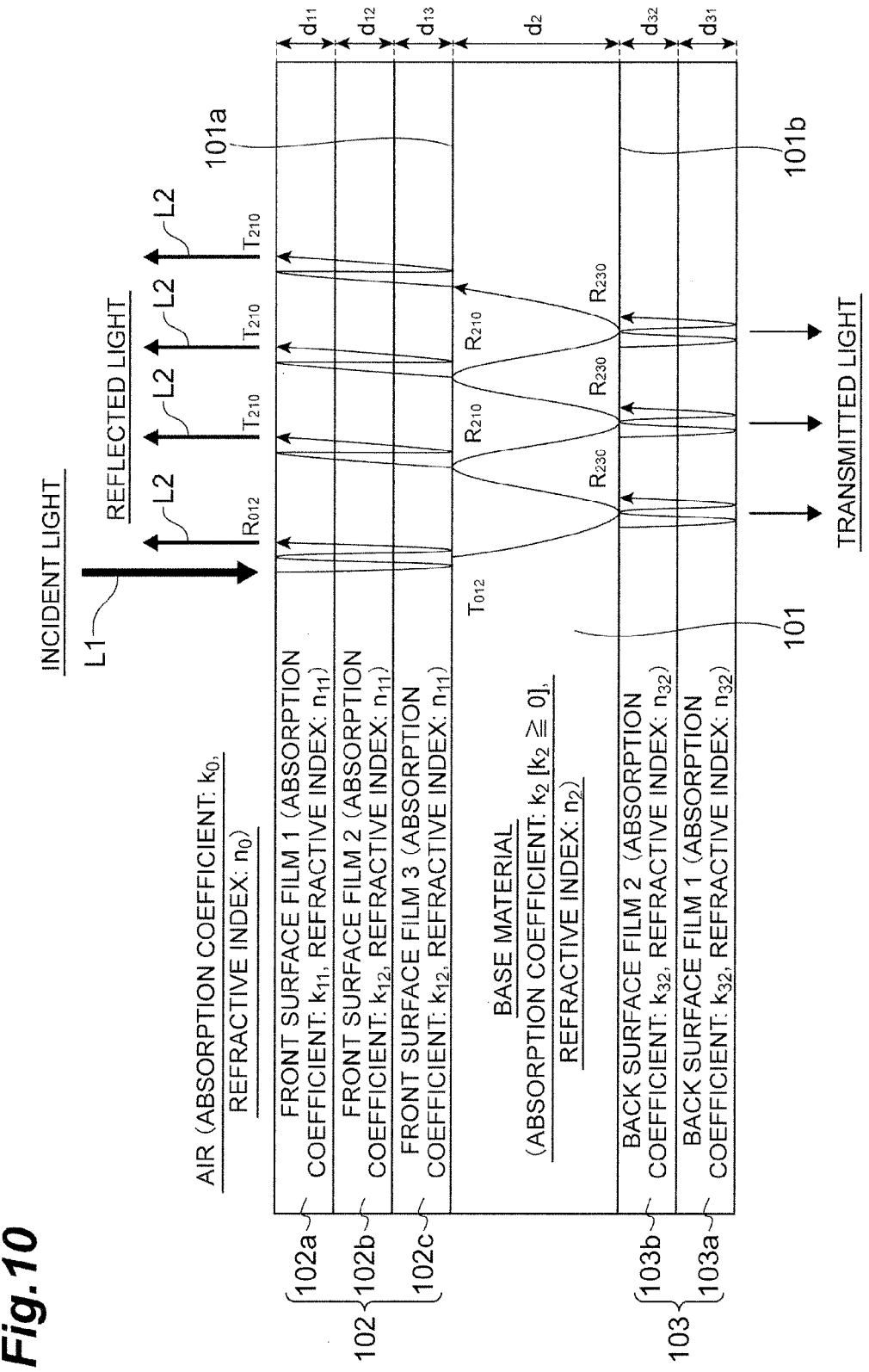
FIG. 10 is a diagram showing definitions of parameters in a first modification of the present invention.

FIG. 10 is a diagram showing definitions of parameters in the present modification, and illustrates a case in which the first film 102 consists of three layers and the second film 103 consists of two layers. As shown in FIG. 10, in the present modification, $k_0$ denotes the extinction coefficient of the periphery (air) of the measurement object 100; $k_{11}$ to $k_{13}$ denote the extinction coefficients of first to third layers 102a to 102c, respectively, of the first film 102; $k_2$ denotes the extinction coefficient of the base material 101 (where $k_2 \geq 0$); and $k_{31}$ and $k_{32}$ denote the extinction coefficients of first and second layers 103a and 103b, respectively, of the second film 103. Also, $n_0$ denotes the refractive index of the periphery (air) of the measurement object 100; $n_{11}$ to $n_{13}$ denote the refractive indices of the first to third layers 102a to 102c, respectively, of the first film 102; $n_2$ denotes the refractive index of the base material 101; and $n_{31}$ and $n_{32}$ denote the refractive indices of the first and second layers 103a and 103b, respectively, of the second film 103. Also, $d_{11}$ to $d_{13}$ denote the layer thicknesses of the first to third layers 102a to 102c, respectively, of the first film 102; $d_2$ denotes the thickness of the base material 101; and $d_{31}$ and $d_{32}$ denote the layer thicknesses of the first and second layers 103a and 103b, respectively, of the second film 103. The definitions of the front surface reflectance values $R_{012}(\lambda)$, $R_{210}(\lambda)$, and $R_{230}(\lambda)$, and the transmissivity values $T_{012}(\lambda)$ and $T_{210}(\lambda)$ are the same as those of the first embodiment.

In this case, the first front surface reflectance $R_{012}(\lambda)$, the second front surface reflectance $R_{210}(\lambda)$, the front surface transmissivity $T_{012}(\lambda)$, and the transmissivity $T_{210}(\lambda)$ through the surface of the first film 102 are expressed as functions of the layer thicknesses $d_{13}$, $d_{12}$, and $d_{13}$ of the layers of the first film 102 by rewriting Expressions (4) to (6) given above, Expressions (7) to (9) given above, Expressions (10) to (12) given above, and Expressions (13) to (15) given above, respectively. Also, the back surface reflectance $R_{230}(\lambda)$ is expressed as a function of the layer thicknesses $d_{31}$ and $d_{32}$ of the layers of the second film 103 by rewriting Expressions (16) to (18) given above. Accordingly, in the present modification, in the same manner as in the case in which each of the first and second films 102 and 103 consists of one layer, the value of the theoretical spectral reflectance $R_{theory}$ closest to the measured spectral reflectance $R_{sig}(\lambda)$ is obtained at step S133, and then at step S134, the values of the layer thicknesses $d_{11}$ to $d_{13}$ are changed to search for the theoretical reflectance $R_{theory012}(\lambda)$ the theoretical reflectance $R_{theory210}(\lambda)$, the theoretical transmissivity $T_{theory012}(\lambda)$, and the theoretical transmissivity $T_{theory210}(\lambda)$ that fit to the first front surface reflectance $R_{012}(\lambda)$, the second front surface reflectance $R_{210}(\lambda)$, the front surface transmissivity $T_{012}(\lambda)$, and the transmissivity $T_{210}(\lambda)$ through the surface of the first film 102 (that is, the surface of the first layer 102a) for the obtained value of the theoretical spectral reflectance $R_{theory}$. Then, the film thickness calculation unit 30A outputs the values of the layer thicknesses $d_{11}$ to $d_{13}$ obtained when the fitting is completed as the layer thicknesses of the first to third layers 102a to 102c, respectively. Also, the film thickness calculation unit 30A changes the values of the layer thicknesses $d_{31}$ and $d_{32}$ to search for the theoretical reflectance $R_{theory230}(\lambda)$ that fits to the back surface reflectance $R_{230}(\lambda)$ for the obtained value of the theoretical spectral reflectance $R_{theory}$. The film thickness calculation unit 30A then outputs the values of the layer thicknesses $d_{31}$ and $d_{32}$ obtained when the fitting is completed as the layer thicknesses of the first and second layers 103a and 103b, respectively.

When each of the first and second films 102 and 103 includes a plurality of layers, the first front surface reflectance $R_{012}(\lambda)$, the second front surface reflectance $R_{210}(\lambda)$, the front surface transmissivity $T_{012}(\lambda)$, the transmissivity $T_{210}(\lambda)$ through the surface of the first film 102, and the back surface reflectance $R_{230}(\lambda)$ change with the layer thicknesses of the layers, and the theoretical spectral reflectance $R_{theory}$ changes accordingly. Hence, when each of the first and second films 102 and 103 includes a plurality of layers as in the case of the present modification, the layer thicknesses $d_{11}$ to $d_{13}$, $d_{31}$, and $d_{32}$ can also be accurately obtained based on the values of the first front surface reflectance $R_{012}(\lambda)$, the second front surface reflectance $R_{210}(\lambda)$, the front surface transmissivity $T_{012}(\lambda)$, the transmissivity $T_{210}(\lambda)$ through the surface of the first film 102, and the back surface reflectance $R_{230}(\lambda)$ for the value of the theoretical spectral reflectance $R_{theory}$ closest to the measured spectral reflectance $R_{sig}(\lambda)$. In the same manner as in the case of the first embodiment, the target of the search by changing the layer thicknesses $d_{11}$ to $d_{13}$ only needs to be at least one of the first front surface reflectance $R_{012}(\lambda)$, the second front surface reflectance $R_{210}(\lambda)$ the front surface transmissivity $T_{012}(\lambda)$, and the transmissivity $T_{210}(\lambda)$ through the surface of the first film 102 for the theoretical spectral reflectance $R_{theory}$. When each of the first and second films 102 and 103 includes a plurality of layers, for example, a plurality of values of the theoretical spectral reflectance $R_{theory}$ may be prepared by changing the layer thicknesses $d_{11}$ to $d_{13}$, $d_{31}$, and $d_{32}$ so as to change the first front surface reflectance $R_{012}(\lambda)$, the second front surface reflectance $R_{210}(\lambda)$, the front surface transmissivity $T_{012}(\lambda)$, the transmissivity $T_{210}(\lambda)$ through the surface of the first film 102, and the back surface reflectance $R_{230}(\lambda)$, and thicknesses of the layers for the theoretical spectral reflectance $R_{theory}$ fitting to the measured spectral reflectance $R_{sig}(\lambda)$ may be determined as the layer thicknesses $d_{11}$ to $d_{13}$, $d_{31}$, and $d_{32}$.

Second Embodiment

Figure 11:
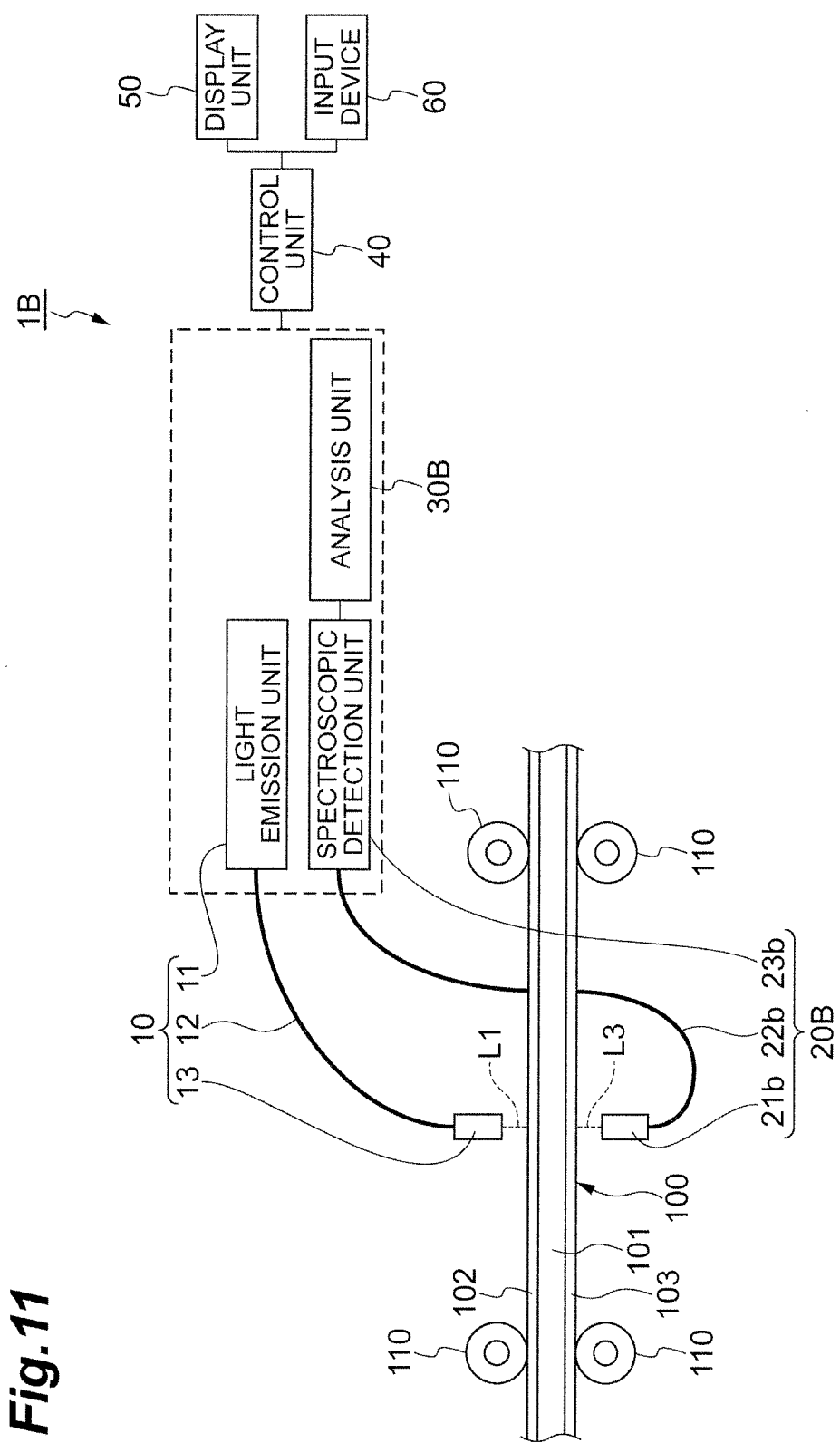
FIG. 11 is a diagram schematically showing the configuration of a film thickness measurement device according to a second embodiment of the present invention.

FIG. 11 is a diagram schematically showing the configuration of a film thickness measurement device 1B according to a second embodiment of the present invention. The film thickness measurement device 1B is a device for measuring the film thickness of the measurement object 100 shown in FIG. 1. As shown in FIG. 11, the film thickness measurement device 1B includes the light emission unit 10, a light detection unit 20B, a film thickness calculation unit 30B, the control unit 40, the display unit 50, and the input device 60. The configurations of the light emission unit 10, the control unit 40, the display unit 50, and the input device 60 are the same as those of the first embodiment. The measurement object 100 may be in the state of being conveyed by the rollers 110 as shown in FIG. 11, or may be stationary.

The light detection unit 20B detects the wavelength-dependent intensity (spectrum) of transmitted light L3 on the back surface 101b side of the measurement object 100. The light detection unit 20B includes a light incident part 21b, a light guiding member 22b, and a spectroscopic detection unit 23b. The transmitted light L3 from the measurement object 100 enters the light incident part 21b. The light incident part 21b is placed in a position facing the second film 103 of the measurement object 100, that is, in a position facing the back surface 101b of the base material 101. The light guiding member 22b is optically coupled at one end thereof with the light incident part 21b, and guides the transmitted light L3 incident to the light incident part 21b. The spectroscopic detection unit 23b is optically coupled with the other end of the light guiding member 22b. The spectroscopic detection unit 23b spectrally separates the transmitted light L3 guided by the light guiding member 22b into wavelength components, and detects the wavelength-dependent intensity of the spectrally separated light. The light guiding member 22b and the spectroscopic detection unit 23b can have the same configurations as those of, for example, the light guiding member 22a and the spectroscopic detection unit 23a of the first embodiment. The spectroscopic detection unit 23b outputs the detected light intensity as an electric signal.

The film thickness calculation unit 30B obtains the film thicknesses of the first and second films 102 and 103 based on the detection result in the light detection unit 20B. In other words, the film thickness calculation unit 30B obtains the film thicknesses of the first and second films 102 and 103 by comparing measured spectral transmissivity that is wavelength-dependent transmissivity obtained based on the detection result in the light detection unit 20B with theoretical spectral transmissivity that is wavelength-dependent theoretical transmissivity, and by fitting the measured and theoretical transmissivity values to each other.

The present embodiment uses a theoretical spectral transmissivity value that takes into account the transmissivity (front surface transmissivity) and the reflectance (front surface reflectance) on the side of the front surface 101a that depends on the refractive index and the film thickness of the first film 102, and that also takes into account the transmissivity (back surface transmissivity) and the reflectance (back surface reflectance) on the side of the back surface 101b that depend on the refractive index and the film thickness of the second film 103. Expression (19) is an expression representing theoretical spectral transmissivity $T_{theory}$ of the present embodiment. The symbol λ represents the wavelength. The definitions of parameters in Expression (19) and expressions for calculating $A_2$ and $R_{210}(\lambda)$ are the same as those of the first embodiment.

Expression (19)

$$T_{theory} = T_{230}(\lambda)T_{012}(\lambda)\exp(-2A_2)\sum_{n=0}^{\infty}[R_{230}(\lambda)R_{210}(\lambda)\exp(-4A_2)]^n \quad (19)$$

As shown in Expression (11), the theoretical spectral transmissivity $T_{theory}$ takes into account transmissivity (back surface transmissivity) $T_{230}(\lambda)$ on the side of the back surface 101b in addition to the transmissivity (front surface transmissivity) $T_{012}(\lambda)$ on the side of the front surface 101a. The theoretical spectral transmissivity $T_{theory}$ also takes into account the multiple reflection component in the base material 101. Specifically, the Σ term on the right-hand side of Expression (19) represents the multiple reflection component in the base material 101, and the multiple reflection component is based on the reflectance (back surface reflectance) $R_{230}(\lambda)$ on the back surface 101b as viewed from the side of the base material 101 and the reflectance (front surface reflectance) $R_{210}(\lambda)$ on the front surface 101a as viewed from the side of the base material 101.

Figure 12:
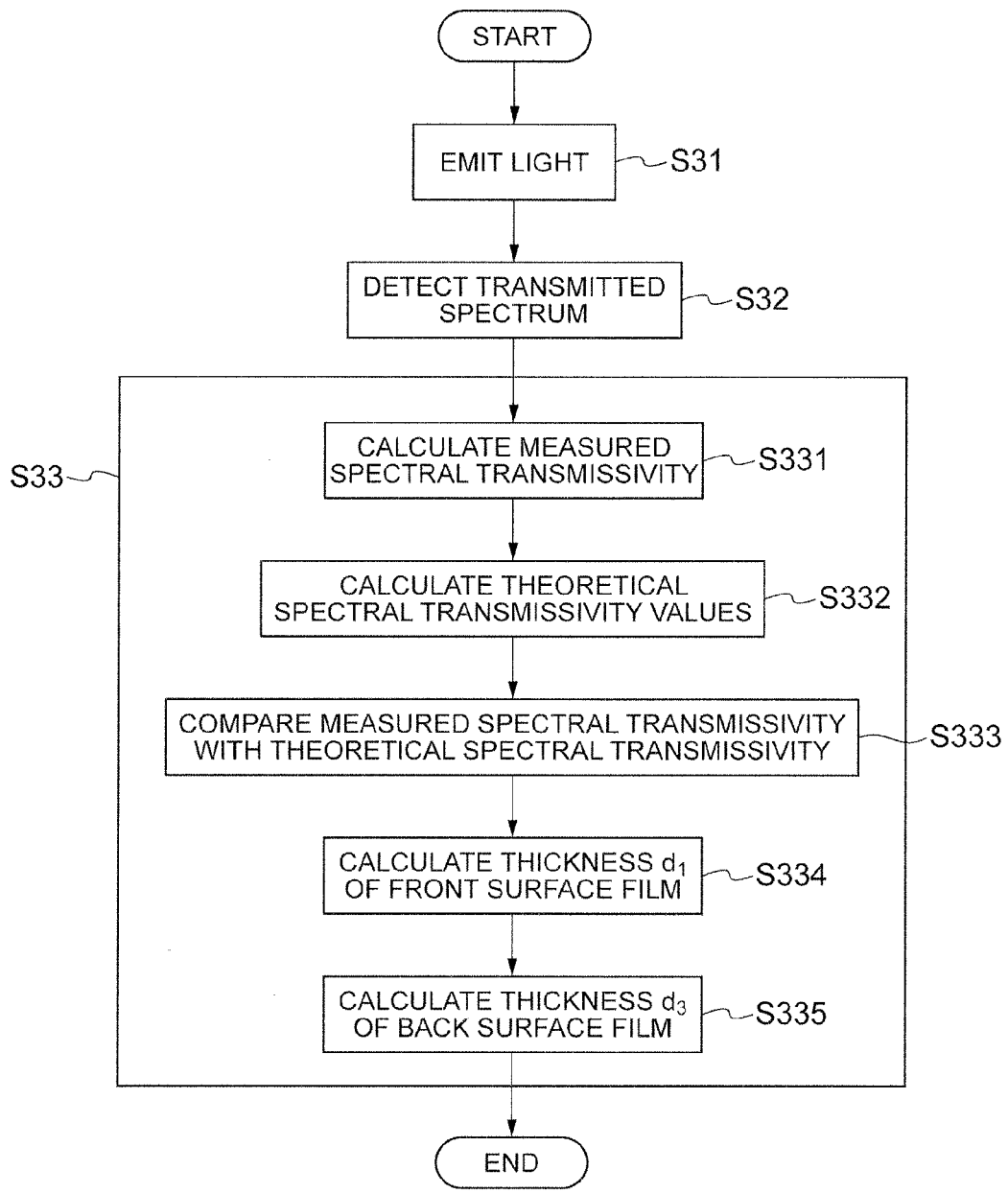
FIG. 12 is a flowchart showing the operation of the film thickness measurement device and a film thickness measurement method according to the second embodiment.

FIG. 12 is a flowchart showing the operation and the film thickness measurement method of the film thickness measurement device 1B according to the present embodiment. As shown in FIG. 12, the light emission unit 10 first emits the incoherent light L1, such as white light, onto the front surface 101a side of the measurement object 100 (light emitting step S31). Then, the light detection unit 20B spectrally separates the transmitted light L3 on the back surface 101b side of the measurement object 100 into the wavelength components, and detects the intensity of each of the wavelength components (light detecting step S32).

Subsequently, the film thickness calculation unit 30B obtains the film thicknesses of the first and second films 102 and 103 (film thickness identifying step S33). At this film thickness identifying step S33, the film thickness calculation unit 30B first calculates the measured spectral transmissivity based on the detection signals from the light detection unit 20B (step S331). For this purpose, the film thickness calculation unit 30B first obtains a transmitted spectrum $S'_{sig}(\lambda)$ from the wavelength-dependent intensity of the transmitted light L3. The film thickness calculation unit 30B then calculates a ratio between a reference transmitted spectrum $S'_{ref}(\lambda)$ obtained in advance using a reference measurement object and the transmitted spectrum $S'_{sig}(\lambda)$, as shown in Expression (20). This ratio is measured spectral transmissivity $T_{sig}(\lambda)$.

Expression (20)

$$T_{sig}(\lambda) = \frac{S'_{sig}(\lambda)}{S'_{ref}(\lambda)} \quad (20)$$

The film thickness calculation unit 30B subsequently calculates the theoretical spectral transmissivity $T_{theory}$ (step S332). First, the operator enters the extinction coefficient $k_2$, the refractive index $n_2$, and the thickness $d_2$ of the base material 101; the extinction coefficient $k_1$ and the refractive index $n_1$ of the first film 102; and the extinction coefficient $k_3$ and the refractive index $n_3$ of the second film 103. The film thickness calculation unit 30B changes each of the values of the front surface transmissivity $T_{012}(\lambda)$, the front surface reflectance $R_{210}(\lambda)$, the back surface transmissivity $T_{230}(\lambda)$, and the reflectance $R_{230}(\lambda)$ that appear in Expression (20), and obtains a plurality of values of the theoretical spectral transmissivity $T_{theory}$ including a combination of a plurality of values of the front surface transmissivity $T_{012}(\lambda)$ and the front surface reflectance $R_{210}(\lambda)$ and a plurality of values of the back surface transmissivity $T_{230}(\lambda)$ and the back surface reflectance $R_{230}(\lambda)$.

The film thickness calculation unit 30B subsequently compares the values of the theoretical spectral transmissivity $T_{theory}$ with the measured spectral transmissivity $T_{sig}(\lambda)$, and obtains the theoretical spectral transmissivity $T_{theory}$ closest (most fitted) to the measured spectral transmissivity $T_{sig}(\lambda)$ (step S333). For example, the least squares method is used at this step S333. Specifically, the film thickness calculation unit 30B obtains the value of the square of the difference between the measured spectral transmissivity $T_{sig}(\lambda)$ and the theoretical spectral transmissivity $T_{theory}$ for each of the values of the theoretical spectral transmissivity $T_{theory}$, and selects the theoretical spectral transmissivity $T_{theory}$ that minimizes the value of the square.

The film thickness calculation unit 30B subsequently calculates the film thickness $d_1$ of the first film 102 based on the theoretical spectral transmissivity $T_{theory}$ closest (most fitted) to the measured spectral transmissivity $T_{sig}(\lambda)$ (step S334). As shown in Expressions (21) to (23) given below, the theoretical front surface transmissivity $T_{theory012}(\lambda)$ is a function of the film thickness $d_1$. In Expressions (21) to (23), $t_{01}$ denotes the amplitude transmission coefficient on the interface between air and the first film 102, and $t_{12}$ denotes the amplitude transmission coefficient on the interface between the first film 102 and the base material 101, where $N_1 = n_1 - ik_1$.

Expression (21)

$$T_{theory012} = \text{Re}\left[\frac{N_2}{N_0}\right]|t_{012}|^2 \quad (21)$$

Expression (22)

$$t_{012} = \frac{t_{01}t_{12}e^{-i\delta_1}}{1 + r_{01}r_{12}e^{-2i\delta_1}} \quad (22)$$

Expression (23)

$$\delta_1 = \frac{2\pi}{\lambda}N_1 d_1 \quad (23)$$

The theoretical front surface reflectance $R_{theory210}(\lambda)$ is also a function of the film thickness $d_1$, as shown in Expressions (24) to (26) given below.

Expression (24)

$$R_{theory210} = |r_{210}|^2 \quad (24)$$

Expression (25)

$$r_{210} = \frac{r_{12} + r_{01}e^{-2i\delta_1}}{1 + r_{12}r_{01}e^{-2i\delta_1}} \quad (25)$$

Expression (26)

$$\delta_1 = \frac{2\pi}{\lambda}N_1 d_1 \quad (26)$$

Accordingly, the film thickness calculation unit 30B uses Expressions (21) to (23) and (24) to (26) to calculate values of the film thickness $d_1$ based on the front surface transmissivity $T_{theory012}(\lambda)$ and the front surface reflectance $R_{theory210}(\lambda)$ for the theoretical spectral transmissivity $T_{theory}$ closest (most fitted) to the measured spectral transmissivity $T_{sig}(\lambda)$, and outputs the mean value of the calculated values as the film thickness of the first film 102 of the measurement object 100.

The film thickness calculation unit 30B also calculates the film thickness $d_3$ of the second film 103 based on the theoretical spectral transmissivity $T_{theory}$ closest (most fitted) to the measured spectral transmissivity $T_{sig}(\lambda)$ (step S335). Theoretical back surface transmissivity $T_{theory230}(\lambda)$ is a function of the film thickness $d_3$, as shown in Expressions (27) to (29) given below. In Expressions (27) to (29), $t_{23}$ denotes the amplitude transmission coefficient on the interface between the base material 101 and the second film 103, and $t_{30}$ denotes the amplitude transmission coefficient on the interface between the second film 103 and air, where $N_3 = n_3 - ik_3$.

Expression (27)

$$T_{theory230} = \text{Re}\left[\frac{N_0}{N_2}\right]|t_{230}|^2 \quad (27)$$

-continued

Expression (28)

$$t_{230} = \frac{t_{23}t_{30}e^{-i\delta_3}}{1 + r_{23}r_{30}e^{-2i\delta_3}} \quad (28)$$

Expression (29)

$$\delta_3 = \frac{2\pi}{\lambda}N_3 d_3 \quad (29)$$

The theoretical back surface reflectance $R_{theory230}(\lambda)$ is also a function of the film thickness $d_3$, as shown in Expressions (30) to (32) given below.

Expression (30)

$$R_{theory230} = |r_{230}|^2 \quad (30)$$

Expression (31)

$$r_{230} = \frac{r_{23} + r_{30}e^{-2i\delta_3}}{1 + r_{23}r_{30}e^{-2i\delta_3}} \quad (31)$$

Expression (32)

$$\delta_3 = \frac{2\pi}{\lambda}N_3 d_3 \quad (32)$$

Accordingly, the film thickness calculation unit 30B uses Expressions (27) to (29) and (30) to (32) to calculate values of the film thickness $d_3$ based on the back surface transmissivity $T_{theory230}(\lambda)$ and the back surface reflectance $R_{theory230}(\lambda)$ for the theoretical spectral transmissivity $T_{theory}$ closest (most fitted) to the measured spectral transmissivity $T_{sig}(\lambda)$, and outputs the mean value of the calculated values as the film thickness of the second film 103 of the measurement object 100.

As described above, at step S33 of the present embodiment, the film thickness calculation unit 30B obtains the film thickness $d_1$ of the first film 102 and the film thickness $d_3$ of the second film 103 by comparing the measured spectral transmissivity $T_{sig}(\lambda)$ obtained based on the detection result at light detecting step S32 with the theoretical spectral transmissivity $T_{theory}$ that takes into account the front surface transmissivity $T_{012}(\lambda)$ and the front surface reflectance $R_{210}(\lambda)$ on the side of the front surface 101a, and that also takes into account the back surface transmissivity $T_{230}(\lambda)$ and the back surface reflectance $R_{230}(\lambda)$ on the side of the back surface 101b. The process at step S334 for calculating the film thickness $d_1$ of the first film 102 and the process at step S335 for calculating the film thickness $d_3$ of the second film 103 can be performed in any order. The process at step S335 may be performed first, or the processes at steps S334 and S335 may be performed in parallel.

In the present embodiment, the example has been shown in which the values of the theoretical spectral transmissivity $T_{theory}$ are calculated in advance, and the measured spectral transmissivity $T_{sig}(\lambda)$ is tried to be fitted to each of the values of the theoretical spectral transmissivity $T_{theory}$. However, the fitting between the theoretical spectral transmissivity $T_{theory}$ and the measured spectral transmissivity $T_{sig}(\lambda)$ is not limited to such a form of fitting. For example, in the same manner as the method shown in FIG. 8, the fitting may be performed in the following manner. Specifically, a value of the theoretical spectral transmissivity $T_{theory}$ is calculated that is constituted by a combination of a value of the front surface transmissivity $T_{012}(\lambda)$, a value of the front surface reflectance $R_{210}(\lambda)$, a value of the back surface transmissivity $T_{230}(\lambda)$ and a value of the back surface reflectance $R_{230}(\lambda)$. This value of the theoretical spectral transmissivity $T_{theory}$ is tried to be fitted to the measured spectral transmissivity $T_{sig}(\lambda)$. If the fitting is not successful (the square of the difference exceeds a threshold), the combination of the values of the front surface transmissivity $T_{012}(\lambda)$, the front surface reflectance $R_{210}(\lambda)$, the back surface transmissivity $T_{230}(\lambda)$, and the back surface reflectance $R_{230}(\lambda)$ is changed, and the changed value of the theoretical spectral transmissivity $T_{theory}$ is tried again to be fitted to the measured spectral transmissivity $T_{sig}(\lambda)$. By repeating the processing described above, a value of the theoretical spectral transmissivity $T_{theory}$ among a plurality of values of the theoretical spectral transmissivity $T_{theory}$ can be obtained that fits to the measured spectral transmissivity $T_{sig}(\lambda)$.

In the present embodiment, the example has been shown in which the film thickness $d_1$ of the first film 102 and the film thickness $d_3$ of the second film 103 are obtained from the value of the front surface transmissivity $T_{012}(\lambda)$, the value of the front surface reflectance $R_{210}(\lambda)$, the value of the back surface transmissivity $T_{230}(\lambda)$, and the value of the back surface reflectance $R_{230}(\lambda)$ for the theoretical spectral transmissivity $T_{theory}$ closest to the measured spectral transmissivity $T_{sig}(\lambda)$. However, the theoretical spectral reflectance $R_{theory}$ may be prepared by changing the value of the film thickness $d_1$ of the first film 102 in Expressions (23) and (26) and the value of the film thickness $d_3$ of the second film 103 in Expressions (29) and (32). Specifically, for example, in the same manner as the method shown in FIG. 9 of the first embodiment, first, a plurality of values of the film thickness $d_1$ of the first film 102 and a plurality of values of the film thickness $d_3$ of the second film 103 may be set; then, for the values of the film thickness $d_1$ and the film thickness $d_3$ thus set, a plurality of values of the front surface transmissivity $T_{012}(\lambda)$, a plurality of values of the front surface reflectance $R_{210}(\lambda)$, a plurality of values of the back surface transmissivity $T_{230}(\lambda)$, and a plurality of values of the back surface reflectance $R_{230}(\lambda)$ may be calculated; and a plurality of values of the theoretical spectral transmissivity $T_{theory}$ may be calculated that correspond to the values of the first front surface transmissivity $T_{012}(\lambda)$, the values of the second front surface reflectance $R_{210}(\lambda)$ the values of the back surface transmissivity $T_{230}(\lambda)$, and the values of the back surface reflectance $R_{230}(\lambda)$ that have been calculated. Alternatively, at step S139 for changing the reflectance and the transmissivity shown in FIG. 7, each value of the reflectance and the transmissivity may be changed by changing the value of the film thickness $d_1$ of the first film 102 and the value of the film thickness $d_3$ of the second film 103. In these cases, the theoretical spectral transmissivity $T_{theory}$ corresponding to a value of the film thickness $d_1$ and a value of the film thickness $d_3$ can be compared with the measured spectral transmissivity $T_{sig}(\lambda)$, so that the value of the film thickness $d_1$ and the value of the film thickness $d_3$ can be determined by obtaining the theoretical spectral transmissivity $T_{theory}$ closet to the measured spectral transmissivity $T_{sig}(\lambda)$ without performing the process at step S134 for calculating the film thickness $d_1$ of the front surface film and the process at step S135 for calculating the film thickness $d_3$ of the back surface film.

The following describes advantageous effects obtained by the film thickness measurement device 1B and the film thickness measurement method according to the present embodiment described above. At the film thickness identifying step S33 in the present embodiment, the film thickness calculation unit 30B compares (fits) the measured spectral transmissivity $T_{sig}(\lambda)$ with the theoretical spectral transmissivity $T_{theory}$ that takes into account the front surface transmissivity $T_{012}(\lambda)$ and the front surface reflectance $R_{210}(\lambda)$ on the side of the front surface 101a, and that also takes into account the back surface transmissivity $T_{230}(\lambda)$ and the back surface reflectance $R_{230}(\lambda)$ on the side of the back surface 101b. The film thickness calculation unit 30B then determines the film thickness $d_1$ of the first film 102 based on a value of the theoretical spectral transmissivity $T_{theory}$ closest to the measured spectral transmissivity $T_{sig}(\lambda)$ among the values of the theoretical spectral transmissivity $T_{theory}$ obtained by changing the front surface transmissivity $T_{012}(\lambda)$ and the front surface reflectance $R_{210}(\lambda)$ on the side of the front surface 101a, and also changing the back surface transmissivity $T_{230}(\lambda)$ and the back surface reflectance $R_{230}(\lambda)$ on the side of the back surface 101b. As a result, the influence of second film 103 on the side of the back surface 101b can be reflected in the theoretical spectral transmissivity $T_{theory}$, so that the film thickness $d_1$ of the first film 102 on the front surface 101a can be accurately measured by taking into account the influence of the thickness and the refractive index of the second film 103 formed on the back surface 101b.

As performed in the present embodiment, the film thickness $d_3$ of the second film. 103 may be determined based on the value of the theoretical spectral transmissivity $T_{theory}$ closest to the measured spectral transmissivity $T_{sig}(\lambda)$. As a result, both the film thickness $d_1$ of the first film 102 on the front surface 101a and the film thickness $d_3$ of the second film 103 on the back surface 101b can be accurately measured by one measurement operation. In this case, the film thickness $d_3$ of the second film 103 may be calculated based on the values of the back surface transmissivity $T_{230}(\lambda)$ and the back surface reflectance $R_{230}(\lambda)$ for the value of the theoretical spectral transmissivity $T_{theory}$ closest to the measured spectral transmissivity $T_{sig}(\lambda)$. The film thickness identifying step S33 or the film thickness calculation unit 30B of the present embodiment calculates the film thickness $d_1$ of the first film 102 and the film thickness $d_3$ of the second film 103, but may calculate only the film thickness $d_1$ of the first film 102.

In the present embodiment, the measured spectral transmissivity $T_{sig}(\lambda)$ and the theoretical spectral transmissivity $T_{theory}$ are directly fitted to each other. However, for example, each of the measured spectral transmissivity $T_{sig}(\lambda)$ and the theoretical spectral transmissivity $T_{theory}$ may be Fourier transformed, and the frequency distribution of the measured spectral transmissivity $T_{sig}(\lambda)$ and the frequency distribution of the theoretical spectral transmissivity $T_{theory}$ may be fitted to each other.

Second Modification

The second embodiment has exemplified the case in which each of the first and second films 102 and 103 consists of one layer. However, when either one or both of the first and second films 102 and 103 includes or include each a plurality of layers, the layer thickness of each of the layers can also be obtained. A second modification of the present invention uses a theoretical spectral transmissivity value that takes into account the transmissivity (front surface transmissivity) and the reflectance (front surface reflectance) on the side of the front surface 101a that depend on the refractive indices and the layer thicknesses of the layers included in the first film 102, and that also takes into account the transmissivity (back surface transmissivity) and the reflectance (back surface reflectance) on the side of the back surface 101b that depend on the refractive indices and the layer thicknesses of the layers included in the second film 103.

Consider the configuration shown in FIG. 10 for the first embodiment. In this case, the theoretical front surface transmissivity $T_{theory012}(\lambda)$ and the theoretical front surface reflectance $R_{theory210}(\lambda)$ are expressed as functions of the layer thicknesses $d_{11}$, $d_{12}$, and $d_{13}$ of the layers of the first film 102 by rewriting Expressions (21) to (26) given above. Also, the theoretical back surface transmissivity $T_{theory230}(\lambda)$ and the theoretical back surface reflectance $R_{theory230}(\lambda)$ are expressed as functions of the layer thicknesses $d_{31}$ and $d_{32}$ of the layers of the second film 103 by rewriting Expressions (27) to (32) given above. Accordingly, in the present modification, in the same manner as in the case in which each of the first and second films 102 and 103 consists of one layer, the value of the theoretical spectral transmissivity $T_{theory}$ closest to the measured spectral transmissivity $T_{sig}(\lambda)$ is obtained at step S333, and then at step S334, the values of the layer thicknesses $d_{11}$ to $d_{13}$ are changed to perform the fitting. Then, values of each of the layer thicknesses $d_{11}$ to $d_{13}$ when the transmissivity $T_{theory012}(\lambda)$ and the reflectance $R_{theory210}(\lambda)$ are closest to the front surface transmissivity $T_{012}(\lambda)$ and the front surface reflectance $R_{210}(\lambda)$, respectively, for the theoretical spectral transmissivity $T_{theory}$ selected at step S333 are calculated, and the mean value or the least-square-estimated value from the values thus calculated is output as each of the layer thicknesses of the first to third layers 102a to 102c, respectively. At step S335, the values of the layer thicknesses $d_{31}$ and $d_{32}$ are changed to perform the fitting. Then, values of each of the layer thicknesses $d_{31}$ and $d_{32}$ when the back surface transmissivity $T_{theory230}(\lambda)$ and the back surface reflectance $R_{theory230}(\lambda)$ are closest to the back surface transmissivity $T_{230}(\lambda)$ and the back surface reflectance $R_{230}(\lambda)$, respectively, for the theoretical spectral transmissivity $T_{theory}$ selected at step S333 are calculated, and the mean value or the least-square-estimated value from the values thus calculated is output as each of the layer thicknesses of the first and second layers 103a and 103b, respectively.

When each of the first and second films 102 and 103 includes a plurality of layers, the front surface transmissivity $T_{012}(\lambda)$, the front surface reflectance $R_{210}(\lambda)$, the back surface transmissivity $T_{230}(\lambda)$, and the back surface reflectance $R_{230}(\lambda)$ change with the layer thicknesses of the layers, and the theoretical spectral transmissivity $T_{theory}$ changes accordingly. Hence, when each of the first and second films 102 and 103 includes a plurality of layers as in the case of the present modification, the layer thicknesses $d_{11}$ to $d_{13}$, $d_{31}$, and $d_{32}$ can also be accurately obtained based on the front surface transmissivity $T_{012}(\lambda)$, the front surface reflectance $R_{210}(\lambda)$, the back surface transmissivity $T_{230}(\lambda)$, and the back surface reflectance $R_{230}(\lambda)$ for the value of the theoretical spectral transmissivity $T_{theory}$ closest to the measured spectral transmissivity $T_{sig}(\lambda)$. In the same manner as in the case of the first embodiment, the target of the search by changing the layer thicknesses $d_{11}$ to $d_{13}$ only needs to be at least one of the front surface transmissivity $T_{012}(\lambda)$ and the front surface reflectance $R_{210}(\lambda)$ for the theoretical spectral transmissivity $T_{theory}$. When each of the first and second films 102 and 103 includes a plurality of layers, for example, a plurality of values of the theoretical spectral reflectance $R_{theory}$ may be prepared by changing the layer thicknesses $d_{11}$ to $d_{13}$, $d_{31}$, and $d_{32}$ so as to change the front surface transmissivity $T_{012}(\lambda)$, the front surface reflectance $R_{210}(\lambda)$, the back surface transmissivity $T_{230}(\lambda)$, and the back surface reflectance $R_{230}(\lambda)$, and thicknesses of the layers for the theoretical spectral reflectance $R_{theory}$ fitting to the measured spectral reflectance $R_{sig}(\lambda)$ may be determined as the layer thicknesses $d_{11}$ to $d_{13}$, $d_{31}$, and $d_{32}$.

The film thickness measurement method and the film thickness measurement device according to the present invention are not limited to the embodiments described above, but may be variously modified. For example, in the embodiments described above, the theoretical spectral reflectance is obtained using Expressions (1) to (3), and the theoretical spectral transmissivity is obtained using Expression (11). However, the expressions for calculating the theoretical spectral reflectance and the theoretical spectral transmissivity are not limited to these expressions, but any expressions can be used.

The first film thickness measurement method and the first film thickness measurement device described above may be characterized in that the film thickness identifying step or the film thickness calculation unit obtains the values of the theoretical spectral reflectance by calculating the value of the front surface reflectance, the value of the front surface transmissivity, and the value of the back surface reflectance for the value of the film thickness of the first film and the value of the film thickness of the second film, and by changing the value of the film thickness of the first film and the value of the film thickness of the second film. As a result, the values of the theoretical spectral reflectance can be suitably obtained.

The first film thickness measurement method and the first film thickness measurement device described above may be characterized in that the film thickness identifying step or the film thickness calculation unit obtains the film thickness of the first film based on at least either one of the value of the front surface reflectance and the value of the front surface transmissivity for the theoretical spectral reflectance closest to the measured spectral reflectance.

The first film thickness measurement method and the first film thickness measurement device described above may be characterized in that the first film includes a plurality of layers, and the film thickness identifying step or the film thickness calculation unit determines the layer thickness of each of the layers of the first film based on the theoretical spectral reflectance closest to the measured spectral reflectance. The second film thickness measurement method and the second film thickness measurement device described above may be characterized in that the first film includes a plurality of layers, and the film thickness identifying step or the film thickness calculation unit determines the layer thickness of each of the layers of the first film based on the theoretical spectral transmissivity closest to the measured spectral transmissivity.

When the first film includes a plurality of layers, the reflectance and the transmissivity on the front surface side change with the layer thicknesses of the layers, and the theoretical spectral reflectance and the theoretical spectral transmissivity change accordingly. Hence, the layer thickness of each of the layers of the first film can be accurately obtained by comparing the values of the theoretical spectral reflectance or the theoretical spectral transmissivity obtained by changing the thickness values of the layers included in the first film with the measured spectral transmissivity or the measured spectral transmissivity.

The first film thickness measurement method and the first film thickness measurement device described above may be characterized in that the film thickness identifying step or the film thickness calculation unit further determines the film thickness of the second film based on the theoretical spectral reflectance closest to the measured spectral reflectance. The second film thickness measurement method and the second film thickness measurement device described above may be characterized in that the film thickness identifying step or the film thickness calculation unit further determines the film thickness of the second film based on the theoretical spectral transmissivity closest to the measured spectral transmissivity. With the methods and the devices described above, the film thicknesses of the first and second films can be accurately measured at the same time by one measurement operation.

The first film thickness measurement method and the first film thickness measurement device described above may be characterized in that the film thickness identifying step or the film thickness calculation unit obtains the value of the film thickness of the second film based on the value of the back surface reflectance for the theoretical spectral reflectance closest to the measured spectral reflectance. As a result, the value of the film thickness of the second film can be suitably obtained.

The first film thickness measurement method and the first film thickness measurement device described above may be characterized in that the second film includes a plurality of layers, and the film thickness identifying step or the film thickness calculation unit determines the layer thickness of each of the layers of the second film based on the theoretical spectral reflectance closest to the measured spectral reflectance. The second film thickness measurement method and the second film thickness measurement device described above may be characterized in that the second film includes a plurality of layers, and the film thickness identifying step or the film thickness calculation unit determines the layer thickness of each of the layers of the second film based on the theoretical spectral transmissivity closest to the measured spectral transmissivity.

When the second film includes a plurality of layers, the reflectance and the transmissivity on the back surface side change with the layer thicknesses of the layers, and the theoretical spectral reflectance and the theoretical spectral transmissivity change accordingly. Hence, the layer thickness of each of the layers of the second film can be accurately obtained by comparing the values of the theoretical spectral reflectance or the theoretical spectral transmissivity obtained by changing the thickness values of the layers included in the second film with the measured spectral transmissivity or the measured spectral transmissivity.

REFERENCE SIGNS LIST 1A, 1B Film thickness measurement device, 10 Light emission unit, 11 Light source, 12 Light guiding member, 13 Light emitting part, 20A, 20B Light detection unit, 21a, 21b Light incident part, 22a; 22b Light guiding member, 23a, 23b Spectroscopic detection unit, 30A, 30B Film thickness calculation unit, 40 Control unit, 50 Display unit, 60 Input device, 100 Measurement object, 101 Base material, 101a Front surface, 101b Back surface, 102 First film, 103 Second film, 110 Roller, L1 Emitted light, L2 Reflected light, L3 Transmitted light.

The invention claimed is:

1. A film thickness measurement method for measuring film thicknesses of a measurement object including a base material having a front surface and a back surface, a first film formed on the front surface, and a second film formed on the back surface, the film thickness measurement method comprising:

emitting light onto the front surface side of the measurement object;

detecting wavelength-dependent intensity of light that is reflected from the measurement object; and determining a film thickness of the first film by comparing measured spectral reflectance that is wavelength-dependent reflectance obtained based on the detection result at the light detecting step with theoretical spectral reflectance that is theoretical wavelength-dependent reflectance and takes into account front surface reflectance being reflectance on the front surface side, front surface transmissivity being transmissivity on the front surface side, and back surface reflectance being reflectance on the back surface side, wherein the determining of the film thickness of the first film includes comparing the measured spectral reflectance with a plurality of values of the theoretical spectral reflectance obtained by changing the value of the front surface reflectance, the value of the front surface transmissivity, and the value of the back surface reflectance, and determining the film thickness of the first film based on a value of the theoretical spectral reflectance closest to the measured spectral reflectance.

2. The film thickness measurement method according to claim 1, wherein the determining of the film thickness of the first film includes obtaining the values of the theoretical spectral reflectance by calculating the value of the front surface reflectance, the value of the front surface transmissivity, and the value of the back surface reflectance for the value of the film thickness of the first film and a value of a film thickness of the second film, and by changing the value of the film thickness of the first film and the value of the film thickness of the second film.

3. The film thickness measurement method according to claim 1, wherein the determining of the film thickness of the first film includes obtaining the value of the film thickness of the first film based on at least either one of the value of the front surface reflectance and the value of the front surface transmissivity for the theoretical spectral reflectance closest to the measured spectral reflectance.

4. The film thickness measurement method according to claim 1,
wherein the first film includes a plurality of layers; and
wherein the determining of the film thickness of the first film includes determining a layer thickness of each of the layers of the first film based on the theoretical spectral reflectance closest to the measured spectral reflectance.

5. The film thickness measurement method according to claim 1, wherein the determining of the film thickness of the first film further includes determining the film thickness of the second film based on the theoretical spectral reflectance closest to the measured spectral reflectance.

6. The film thickness measurement method according to claim 1, wherein the determining of the film thickness of the first film includes obtaining the value of the film thickness of the second film based on the value of the back surface reflectance for the theoretical spectral reflectance closest to the measured spectral reflectance.

7. The film thickness measurement method according to claim 1,
wherein the second film includes a plurality of layers; and
wherein the determining of the film thickness of the first film further includes determining a layer thickness of each of the layers of the second film based on the theoretical spectral reflectance closest to the measured spectral reflectance.

8. A film thickness measurement method for measuring film thicknesses of a measurement object including a base material having a front surface and a back surface, a first film formed on the front surface, and a second film formed on the back surface, the film thickness measurement method comprising:

emitting light onto the front surface side of the measurement object;

detecting wavelength-dependent intensity of light that is transmitted through the measurement object; and determining a film thickness of the first film by comparing measured spectral transmissivity that is wavelength-dependent transmissivity obtained based on the detection result at the light detecting step with theoretical spectral transmissivity that is theoretical wavelength-dependent transmissivity and takes into account front surface transmissivity being transmissivity on the front surface side, front surface reflectance being reflectance on the front surface side, back surface transmissivity being transmissivity on the back surface side, and back surface reflectance being reflectance on the back surface side, wherein the determining of the film thickness of the first film includes comparing the measured spectral transmissivity with a plurality of values of the theoretical spectral transmissivity obtained by changing each of the value of the front surface transmissivity, the value of the front surface reflectance, the value of the back surface transmissivity, and the value of the back surface reflectance, and determining the film thickness of the first film based on a value of the theoretical spectral transmissivity closest to the measured spectral transmissivity.

9. The film thickness measurement method according to claim 8,
wherein the first film includes a plurality of layers; and
wherein the determining of the film thickness of the first film includes determining a layer thickness of each of the layers of the first film based on the theoretical spectral transmissivity closest to the measured spectral transmissivity.

10. The film thickness measurement method according to claim 8, wherein the determining of the film thickness of the first film further includes determining the film thickness of the second film based on the theoretical spectral transmissivity closest to the measured spectral transmissivity.

11. The film thickness measurement method according to claim 8,
wherein the second film includes a plurality of layers; and
wherein the determining of the film thickness of the first film includes determining a layer thickness of each of the layers of the second film based on the theoretical spectral transmissivity closest to the measured spectral transmissivity.

12. A film thickness measurement device for measuring film thicknesses of a measurement object including a base material having a front surface and a back surface, a first film formed on the front surface, and a second film formed on the back surface, the film thickness measurement device comprising:

a light source configured to emit light to be irradiated the front surface side of the measurement object;

a light detector configured to detect wavelength-dependent intensity of light that is reflected from the measurement object and output a detection signal corresponding to the wavelength-dependent intensity; and a calculator connected to the light detector, and configured to input the detection signal and determine a film thickness of the first film by comparing measured spectral reflectance that is wavelength-dependent reflectance obtained based on the detection signal with theoretical spectral reflectance that is wavelength-dependent theoretical reflectance and takes into account front surface reflectance being reflectance on the front surface side, front surface transmissivity being transmissivity on the front surface side, and back surface reflectance being reflectance on the back surface side, wherein the calculator is configured to compare the measured spectral reflectance with a plurality of values of the theoretical spectral reflectance obtained by changing each of the value of the front surface reflectance, the value of the front surface transmissivity, and the value of the back surface reflectance, and to determine the film thickness of the first film based on a value of the theoretical spectral reflectance closest to the measured spectral reflectance.

13. The film thickness measurement device according to claim 12, wherein the calculator is configured to obtain the values of the theoretical spectral reflectance by calculating the value of the front surface reflectance, the value of the front surface transmissivity, and the value of the back surface reflectance for the value of the film thickness of the first film and a value of a film thickness of the second film, and by changing the value of the film thickness of the first film and the value of the film thickness of the second film.

14. The film thickness measurement device according to claim 12, wherein the calculator is configured to obtain the value of the film thickness of the first film based on at least either one of the value of the front surface reflectance and the value of the front surface transmissivity for the theoretical spectral reflectance closest to the measured spectral reflectance.

15. The film thickness measurement device according to claim 12,
wherein the first film includes a plurality of layers; and
wherein the calculator is configured to determine a layer thickness of each of the layers of the first film based on the value of the theoretical spectral reflectance closest to the measured spectral reflectance.

16. The film thickness measurement device according to claim 12, wherein the calculator is configured to further obtain the film thickness of the second film based on the value of the theoretical spectral reflectance closest to the measured spectral reflectance.

17. The film thickness measurement device according to claim 12,
wherein the second film includes a plurality of layers; and
wherein the calculator is configured to determine a layer thickness of each of the layers of the second film based on the value of the theoretical spectral reflectance closest to the measured spectral reflectance.

18. A film thickness measurement device for measuring film thicknesses of a measurement object including a base material having a front surface and a back surface, a first film formed on the front surface, and a second film formed on the back surface, the film thickness measurement device comprising:

a light source configured to emit light onto the front surface side of the measurement object;

a light detector configured to detect wavelength-dependent intensity of light that is transmitted through the measurement object and outputting a detection signal corresponding to the wavelength-dependent intensity; and a calculator connecting to the light detector, and configured to input the detection signal and determine a film thickness of the first film by comparing measured spectral transmissivity that is wavelength-dependent transmissivity obtained based on the detection signal with theoretical spectral transmissivity that is wavelength-dependent theoretical transmissivity and takes into account front surface transmissivity being transmissivity on the front surface side, front surface reflectance being reflectance on the front surface side, back surface transmissivity being transmissivity on the back surface side, and back surface reflectance being reflectance on the back surface side, wherein the calculator is configured to compare the measured spectral transmissivity with a plurality of values of the theoretical spectral transmissivity obtained by changing each of the value of the front surface transmissivity, the value of the front surface reflectance, the value of the back surface transmissivity, and the value of the back surface reflectance, and to determine the film thickness of the first film based on a value of the theoretical spectral transmissivity closest to the measured spectral transmissivity.

19. The film thickness measurement device according to claim 18,
wherein the first film includes a plurality of layers; and
wherein the calculator is configured to determine a layer thickness of each of the layers of the first film based on the theoretical spectral transmissivity closest to the measured spectral transmissivity.

20. The film thickness measurement device according to claim 18, wherein the calculator is configured to further determine the film thickness of the second film based on the theoretical spectral transmissivity closest to the measured spectral transmissivity.

21. The film thickness measurement device according to claim 18,
wherein the second film includes a plurality of layers; and
wherein the calculator is configured to determine a layer thickness of each of the layers of the second film based on the theoretical spectral transmissivity closest to the measured spectral transmissivity.

* * * * *